(12) United States Patent
Bendett et al.

(10) Patent No.: US 8,632,577 B1
(45) Date of Patent: *Jan. 21, 2014

(54) HYBRID OPTICAL-ELECTRICAL PROBES FOR STIMULATION OF NERVE OR OTHER ANIMAL TISSUE

(71) Applicant: Lockheed Martin Corporation, Bethesda, MD (US)

(72) Inventors: Mark P. Bendett, Connell Hill, NJ (US); James S. Webb, Seattle, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,304

(22) Filed: Jan. 22, 2013

Related U.S. Application Data

(62) Division of application No. 13/022,576, filed on Feb. 7, 2011, now Pat. No. 8,357,187, which is a division of application No. 12/018,185, filed on Jan. 22, 2008, now Pat. No. 7,883,536.

(60) Provisional application No. 60/885,879, filed on Jan. 19, 2007, provisional application No. 60/964,634, filed on Aug. 13, 2007.

(51) Int. Cl.
  *A61N 1/05* (2006.01)
(52) U.S. Cl.
  USPC .............................................. 607/88; 607/89
(58) Field of Classification Search
  USPC ...................................... 607/88, 89, 116, 122
  See application file for complete search history.

(56) References Cited

U.S. PATENT DOCUMENTS

| | | |
|---|---|---|
| 4,064,872 A | 12/1977 | Caplan |
| 4,215,694 A | 8/1980 | Isakov et al. |
| 4,296,995 A | 10/1981 | Bickel |
| 4,400,590 A | 8/1983 | Michelson |
| 4,504,970 A | 3/1985 | Werth et al. |
| 4,541,115 A | 9/1985 | Werth |
| 4,550,431 A | 10/1985 | Werth et al. |
| 4,551,850 A | 11/1985 | Werth et al. |
| 4,558,703 A | 12/1985 | Mark |
| 4,566,935 A | 1/1986 | Hornbeck |
| 4,596,992 A | 6/1986 | Hornbeck |
| 4,671,285 A | 6/1987 | Walker |

(Continued)

FOREIGN PATENT DOCUMENTS

WO    WO 0025112    5/2000

OTHER PUBLICATIONS

Allegre, et al., "Stimulation in the rat of a nerve fiber bundle by a short UV pulse from an excimer laser", "NeuroScience Letters", 1994, pp. 261-264, vol. 180.

(Continued)

*Primary Examiner* — Bill Thomson
*Assistant Examiner* — Jeffrey Lipitz
(74) *Attorney, Agent, or Firm* — Charles A. Lemaire; Jonathan M. Rixen; Lemaire Patent Law Firm, P.L.L.C.

(57) ABSTRACT

An optical-signal vestibular-nerve stimulation device and method that provides different nerve stimulation signals to a plurality of different vestibular nerves, including at least some of the three semicircular canal nerves and the two otolith organ nerves. In some embodiments, balance conditions of the person are sensed by the implanted device, and based on the sensed balance conditions, varying infrared (IR) nerve-stimulation signals are sent to a plurality of the different vestibular nerves.

23 Claims, 10 Drawing Sheets

(56) References Cited

U.S. PATENT DOCUMENTS

| | | |
|---|---|---|
| 4,681,791 A | 7/1987 | Shibahashi et al. |
| 4,720,189 A | 1/1988 | Heynen et al. |
| 4,724,835 A | 2/1988 | Liss et al. |
| 4,757,515 A | 7/1988 | Hughes |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,473,707 A | 12/1995 | Werth |
| 5,473,708 A | 12/1995 | Werth |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,820,625 A | 10/1998 | Izawa et al. |
| 5,827,265 A | 10/1998 | Glinsky et al. |
| 5,851,223 A | 12/1998 | Liss et al. |
| 5,899,865 A | 5/1999 | Chance |
| 5,913,884 A | 6/1999 | Trauner et al. |
| 6,033,431 A | 3/2000 | Segal |
| 6,048,359 A | 4/2000 | Biel |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,240,308 B1 | 5/2001 | Hardy et al. |
| 6,246,892 B1 | 6/2001 | Chance |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,324,429 B1 | 11/2001 | Shire et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,421,474 B2 | 7/2002 | Jewell et al. |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,488,704 B1 | 12/2002 | Connelly et al. |
| 6,493,476 B2 | 12/2002 | Bendett |
| 6,505,075 B1 | 1/2003 | Weiner |
| 6,542,530 B1 | 4/2003 | Shieh et al. |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,736,807 B2 | 5/2004 | Yamazaki et al. |
| 6,744,548 B2 | 6/2004 | Abeles |
| 6,746,473 B2 | 6/2004 | Shanks et al. |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,920,358 B2 | 7/2005 | Greenberg et al. |
| 6,921,413 B2 | 7/2005 | Mahadevan-Jansen et al. |
| 6,953,341 B2 | 10/2005 | Black |
| 6,956,650 B2 | 10/2005 | Boas et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,010,341 B2 | 3/2006 | Chance |
| 7,010,356 B2 | 3/2006 | Jog et al. |
| 7,031,363 B2 | 4/2006 | Biard et al. |
| 7,040,805 B1 | 5/2006 | Ou et al. |
| 7,068,878 B2 | 6/2006 | Crossman-Bosworth et al. |
| 7,069,083 B2 | 6/2006 | Finch |
| 7,079,900 B2 | 7/2006 | Greenburg et al. |
| 7,085,300 B2 | 8/2006 | Werner et al. |
| 7,095,770 B2 | 8/2006 | Johnson |
| 7,116,886 B2 | 10/2006 | Colgan et al. |
| 7,131,968 B2 | 11/2006 | Bendett et al. |
| 7,139,603 B2 | 11/2006 | Chance |
| 7,156,866 B1 | 1/2007 | Riggs et al. |
| 7,160,289 B2 | 1/2007 | Cohen |
| 7,177,081 B2 | 2/2007 | Tomita et al. |
| 7,190,993 B2 | 3/2007 | Sharma et al. |
| 7,194,063 B2 | 3/2007 | Dilmanian et al. |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,309,335 B2 | 12/2007 | Altshuler et al. |
| 7,311,722 B2 | 12/2007 | Larsen |
| 7,324,852 B2 | 1/2008 | Barolat et al. |
| 7,329,251 B2 | 2/2008 | Yamada et al. |
| 7,337,004 B2 | 2/2008 | Classen et al. |
| 7,351,241 B2 | 4/2008 | Bendett et al. |

(56) References Cited

U.S. PATENT DOCUMENTS

| | | | |
|---|---|---|---|
| 7,391,561 B2 | 6/2008 | Di Teodoro et al. |
| 7,402,167 B2 | 7/2008 | Nemenov |
| RE40,587 E | 11/2008 | McKinnon |
| 7,488,341 B2 | 2/2009 | Merfeld |
| 7,598,088 B2 | 10/2009 | Balas |
| 7,647,112 B2 | 1/2010 | Tracey et al. |
| 7,654,750 B2 | 2/2010 | Brenner et al. |
| 7,736,382 B2 | 6/2010 | Webb et al. |
| 7,747,318 B2 | 6/2010 | John et al. |
| 7,756,588 B2 | 7/2010 | Jog et al. |
| 7,771,374 B2 | 8/2010 | Slatkine |
| 7,776,631 B2 | 8/2010 | Miles |
| 7,787,170 B2 | 8/2010 | Patel et al. |
| 7,792,588 B2 | 9/2010 | Harding |
| 7,797,029 B2 | 9/2010 | Gibson et al. |
| 7,801,601 B2 | 9/2010 | Maschino et al. |
| 7,803,454 B2 | 9/2010 | Toepel |
| 7,833,257 B2 | 11/2010 | Walsh, Jr. et al. |
| 7,873,085 B2 | 1/2011 | Babushkin et al. |
| 7,883,535 B2 | 2/2011 | Cantin et al. |
| 7,883,536 B1 | 2/2011 | Bendett et al. |
| 7,894,905 B2 | 2/2011 | Pless et al. |
| 7,899,512 B2 | 3/2011 | Labadie et al. |
| 7,908,010 B2 | 3/2011 | Greenberg et al. |
| 7,914,842 B1 | 3/2011 | Greenberg et al. |
| 7,951,181 B2 | 5/2011 | Mahadevan-Jansen et al. |
| 7,962,192 B2 | 6/2011 | Bodduluri |
| 7,988,688 B2 | 8/2011 | Webb et al. |
| 8,012,189 B1 | 9/2011 | Webb et al. |
| 8,078,263 B2 | 12/2011 | Zeman et al. |
| 8,136,531 B2 | 3/2012 | Chariff |
| 8,197,539 B2 | 6/2012 | Nasiatka et al. |
| 8,207,211 B2 | 6/2012 | Wharton et al. |
| 8,372,127 B2 | 2/2013 | Merfeld |
| 8,398,692 B2 | 3/2013 | Zhang et al. |
| 2002/0002391 A1 | 1/2002 | Gerdes |
| 2003/0236458 A1 | 12/2003 | Hochman |
| 2004/0225339 A1 | 11/2004 | Yaroslavsky et al. |
| 2005/0099824 A1 | 5/2005 | Dowling et al. |
| 2005/0143789 A1 | 6/2005 | Whitehurst et al. |
| 2006/0161218 A1 | 7/2006 | Danilov |
| 2006/0167564 A1 | 7/2006 | Flaherty et al. |
| 2006/0276861 A1 | 12/2006 | Lin |
| 2007/0053996 A1 | 3/2007 | Boyden et al. |
| 2007/0054319 A1 | 3/2007 | Boyden et al. |
| 2007/0191906 A1 | 8/2007 | Iyer et al. |
| 2007/0261127 A1 | 11/2007 | Boyden et al. |
| 2008/0009748 A1 | 1/2008 | Gratton et al. |
| 2008/0077200 A1 | 3/2008 | Bendett et al. |
| 2008/0161697 A1 | 7/2008 | Chance |
| 2008/0299201 A1 | 12/2008 | Kozloski et al. |
| 2009/0030327 A1 | 1/2009 | Chance |
| 2009/0099441 A1 | 4/2009 | Giszter et al. |
| 2009/0163982 A1 | 6/2009 | deCharms |

OTHER PUBLICATIONS

Arora, Komal, et al., "Electrical stimulation rate effects on speech perception in cochlear implants", "International Journal of Audiology", 2009, pp. 561-567, vol. 48.

Arridge, et al., "The theoretical basis for the determination of optical pathlengths in tissue: temporal and frequency analysis", "Phys. Med. Biol.", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Boyden, Edward S., et al., "Millisecond-timescale, genetically targeted optical control of neural activity", "Nature Neuroscience ", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregularion of Biol. Activity by Photochromic Reagents, 3. Photoreg. of Bioelectricity by Acetylcholine Receptor Inh", "Proc. Natl. Acad. Sci.", 1969, pp. 1230-1234, vol. 64, No. 4.

Dodt, H.-U., et al., "Precisely Localized LTD in the Neocortex Revealed by Infrared-Guided Laser Stimulation.", "Science ", Oct. 1, 1999, pp. 110-113, vol. 286.

Dodt, H.-U., et al., "Circuitry of rat barrel cortex investigated by infrared-guided laser stimulation", "NeuroReport", Mar. 24, 2003, pp. 623-627, vol. 14, No. 4.

Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Fork, Richard L., "Laser Stimulation of Nerve Cells in Aplysia", "Science, New Series", Mar. 5, 1971, pp. 907-908, vol. 171, No. 3974.

Fu, Qian-Jie, et al., "Effect of Stimulation Rate on Phoneme Recognition by Nucleus-22 Cochlear Implant Listeners", "J. Acoust. Soc. Am.", Jan. 2000, pp. 589-597, vol. 107, No. 1.

Fu, Qian-Jie, et al., "Effects of Dynamic Range and Amplitude Mapping on Phoneme Recognition in Nucleus-22 Cochlear Implant Users", "Ear and Hearing", 2000, pp. 227-235, vol. 21.

Harner, et al., "Improved Preservation of Facial Nerve Function With Use of Electrical Monitoring During Removal of Acoustic Neuromas", "Mayo Clinic Proceedings. Mayo Clinic", Feb. 1987, pp. 92-102, vol. 62.

Heinz, Michael G., et al, "Response Growth with Sound Level in Auditory-Nerve Fibers After Noise-Induced Hearing Loss", "J. Neurophysiology", 2004, pp. 784-795, vol. 91.

Izzo, et al., "Laser Stimulation of the Auditory Nerve", "Lasers in Surgery and Medicine", 2006, Publisher: Wiley-Liss, Inc.

Loizou, Philipos C., "Speech Processing in Vocoder-Centric Cochlear Implants", "Adv. Oto-Rhino-Laryngolog", 2006, pp. 109-143, vol. 64.

Maiorov, M., et al., "218 W quasi-CW operation of 1.83 um two-dimensional laser diode array", "Electronics Letters", Apr. 15, 1999, pp. 636-638, vol. 35, No. 8.

Makeieff, et al., "Continuous Facial Nerve Monitoring During Pleomorphic Adenoma Recurrence Surgery", "The Laryngoscope", Jul. 2005, pp. 1310-1314.

Matthies, et al., "Direct Brainstem Recording of Auditory Evoked Potentials During Vestibular Schwannoma Resection: Nuclear BAEP Recording", "J. Neurosurg.", Jun. 1997, pp. 1057-1062, vol. 86.

McKay, et al., "Loudness Perception with Pulsatile Electrical Stimulation: The Effect of Interpulse Intervals", 1998.

McKay, et al., "Loudness Summation for Pulsatile Electrical Stimulation of the Cochlea: Effects of Rate, Electrode Separation, Level, an", "J. Acoust. Soc. Am.", Sep. 2001, pp. 1514-1524, vol. 110.

Meier, et al, "Continuous Intraoperative Facial Nerve Monitoring in Predicting Postoperative Injury During Parotidectomy", "The Laryngoscope", Sep. 2006, pp. 1569-1572, vol. 116.

Moller, Aage R., "History of Cochlear Implants and Auditory Brainstem Implants", "Adv Otorhinolaryngol. Basel, Karger", 2006, pp. 1-10, vol. 64.

Moller, et al., "Intraoperative Neurophysiologic Monitoring", "American Journal of Otology", Jan. 1995, pp. 115-117, vol. 16, No. 1.

Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004 , pp. 145-150, vol. 101.

(56) References Cited

OTHER PUBLICATIONS

Naples, et al., "A spiral nerve cuff electrode for peripheral nerve stimulation", "IEEE Trans Biomed Eng", Nov. 1988, pp. 905-916, vol. 35, No. 11.
Nelson, et al., "Intensity Discrimination as a Function of Stimulus Level with Electric Stimulation", "J. Acoust. Soc. Am.", Oct. 1996, pp. 2393-2414, vol. 100.
Passos, D., et al., "Tissue phantom for optical diagnostics based on a suspension of microspheres with a fractal size distribution", "Journal of Biomedical Optics.", Nov.-Dec. 2005, pp. 064036, vol. 10, No. 6.
Princeton Lightwave (Company), "High Power Multimode Laser Arrays", "www.princetonlightwave.com/content/pli_high_power_multimode_laser_arrays.pdf", Dec. 24, 2005 downloaded.
Princeton Lightwave (Company), "High Power Water Cooled Laser Stack", "http://www.princetonlightwave.com/content/pli_high_power_multimode_laser_stacks.pdf", Oct. 24, 2005 downloaded.
Princeton Lightwave (Company), "High Power Single Element Laser", "www.princetonlightwave.com/content/HP%20Single%20Element%20Laser%20version%202.pdf", 2005 (downloaded).
Rolfe, "In Vivo Near-Infrared Spectroscopy", "Annu. Rev. Biomed. Eng.", 2000, pp. 715-754, vol. 2.
Tarler, et al., "Comparison of joint torque evoked with monopolar and tripolar-cuff electrodes", "IEEE Trans Neural Syst Rehabil Eng", 2003, pp. 227-235, vol. 11, No. 3.
Tonn, et al., "Acoustic Neuroma Surgery as an Interdisciplinary Approach: A Neurosurgical Series of 508 Patients", "Journal of Neurology, Neurosurgery and Psychiatry", Aug. 2000, pp. 161-166, vol. 69, No. 2.
Vandali, et al., "Speech Perception as a Function of Electrical Stimulation Rate: Using the Nucleus 24 Cochlear Implant", Dec. 2000.
Vogel, Alfred, et al., "Mechanisms of pulsed laser ablation of biological tissues.", "Chemical Reviews", 2003, pp. 577-644, vol. 103, No. 2.
Wells, Jonathon, et al., "Application of Infrared Light for in vivo Neural Stimulation.", "Journal of Biomedical Optics", Nov. 2005, pp. 064003-1 to 064003-12, vol. 10, No. 6.
Wells, Jonathon, et al., "Optical stimulation of neural tissue in vivo", "Optics Letters", Mar. 1, 2005, pp. 504-506, vol. 30, No. 5.
Witt, Robert L., "Facial Nerve Monitoring in Parotid Surgery: The Standard of Care?", "Otolaryngology—Head and Neck Surgery", Nov. 1998, pp. 468-470, vol. 119, No. 5.
Yoo, et al., "Selective recording of the canine hypoglossal nerve using a multicontact flat interface nerve electrode", "IEEE Trans Biomed Eng", Aug. 2005, pp. 1461-1469, vol. 52, No. 8.
Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.
Zhang, Feng, et al., "Channelrhodopsin-2 and optical control of excitable cells", "Nature Methods", Sep. 21, 2006, pp. 785-792, vol. 3, No. 10.

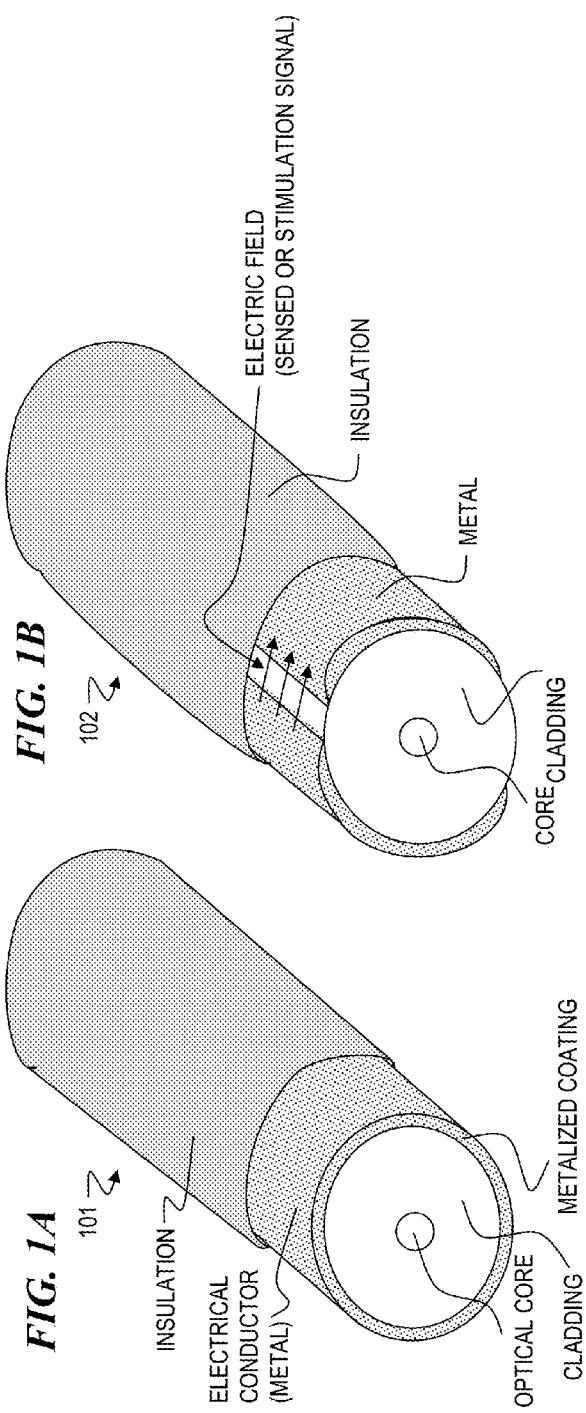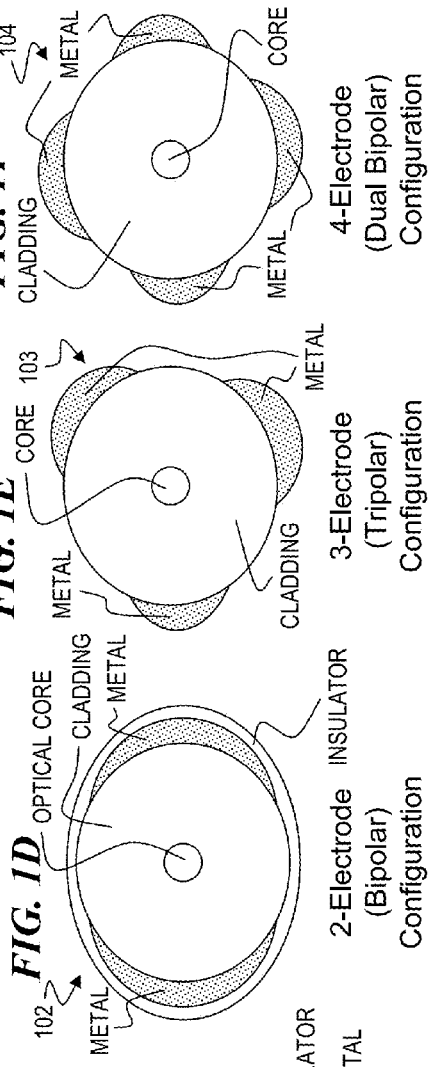

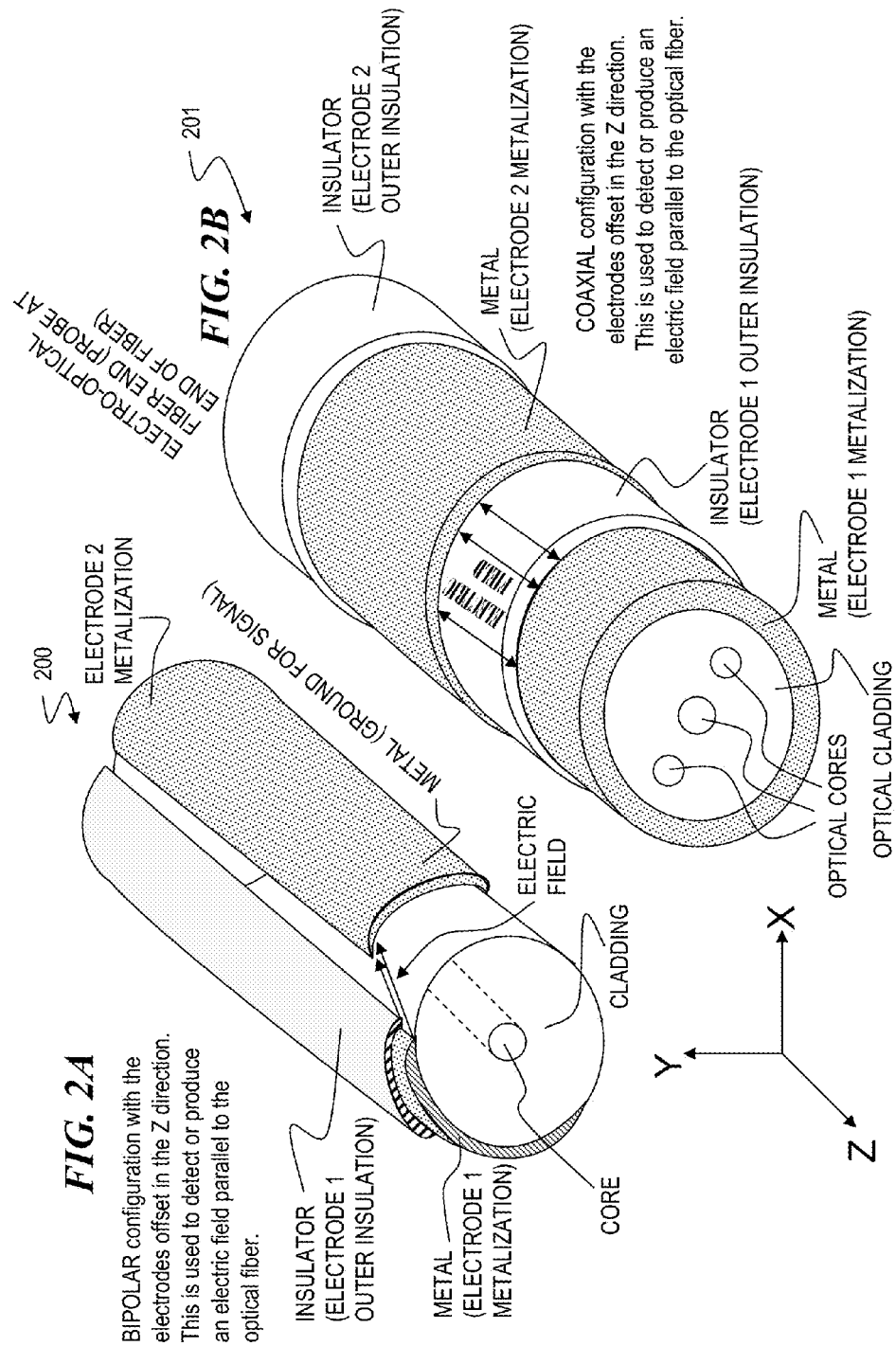

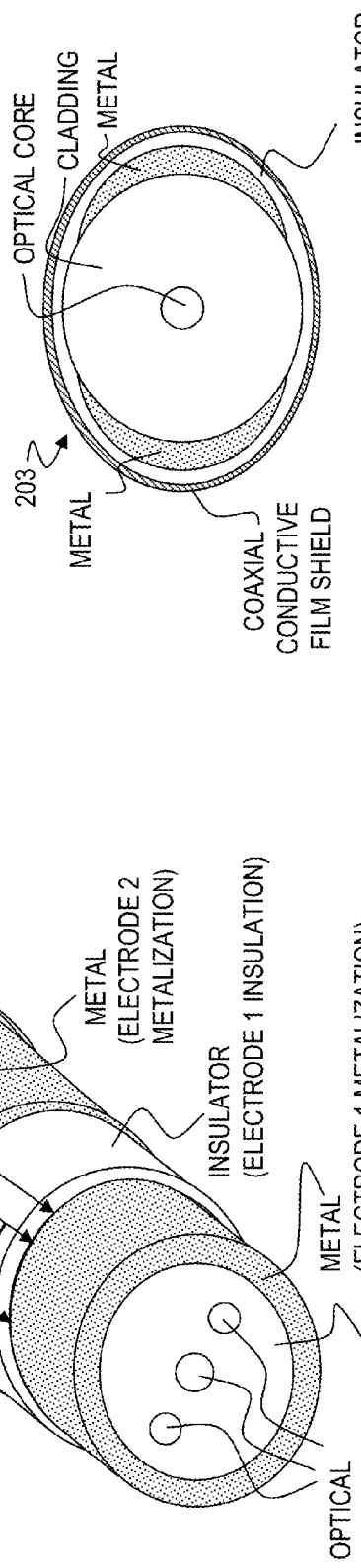
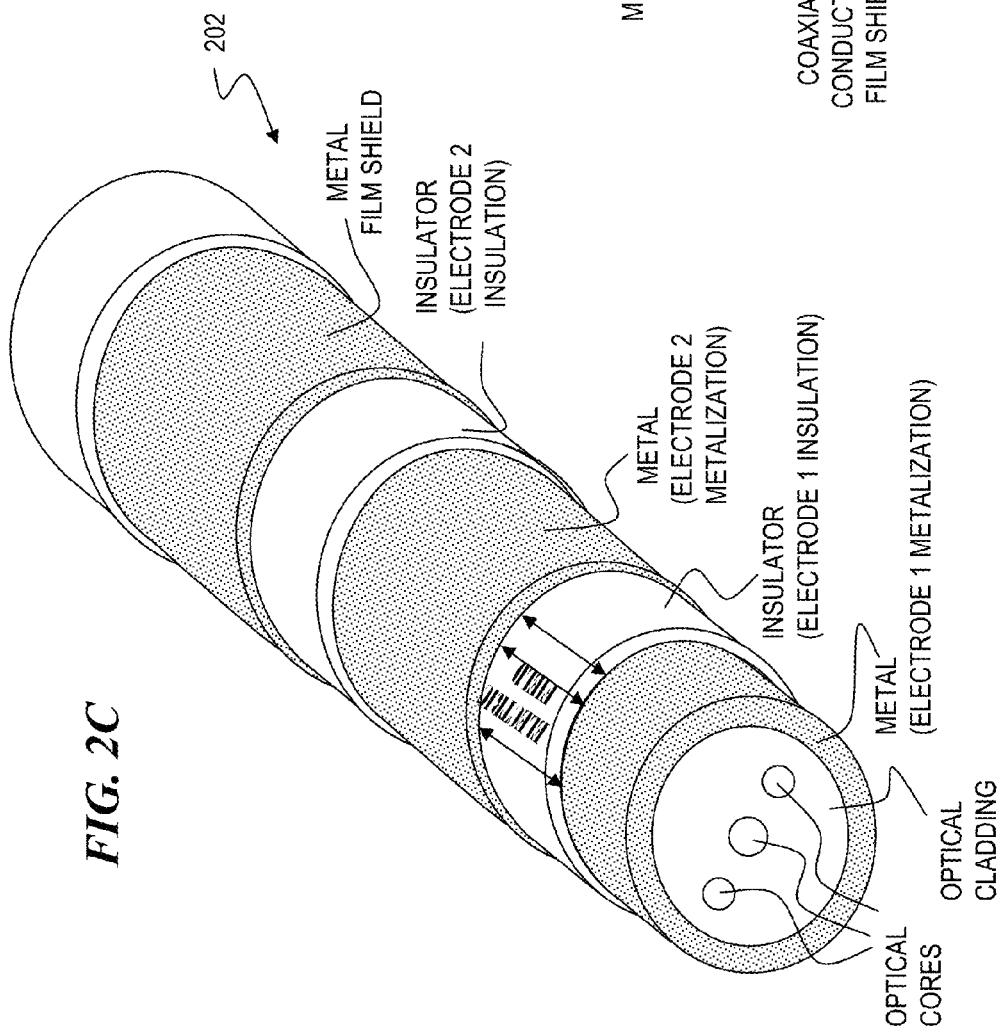
FIG. 2C
FIG. 2D

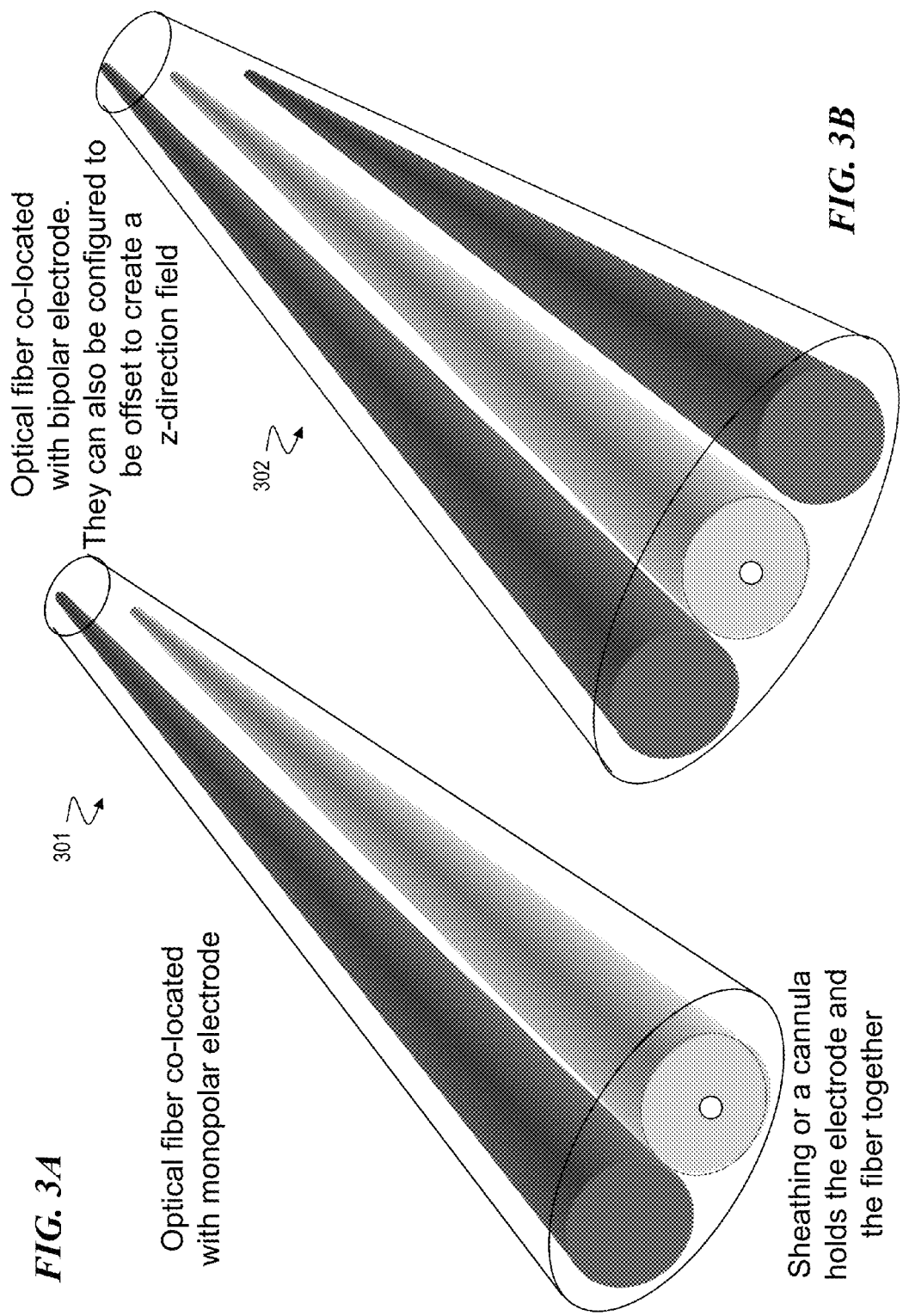

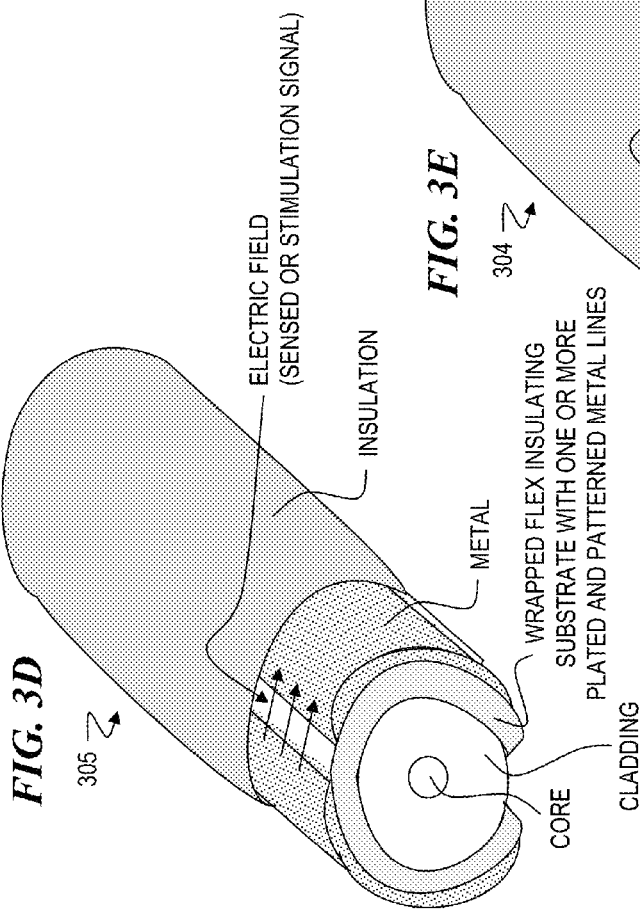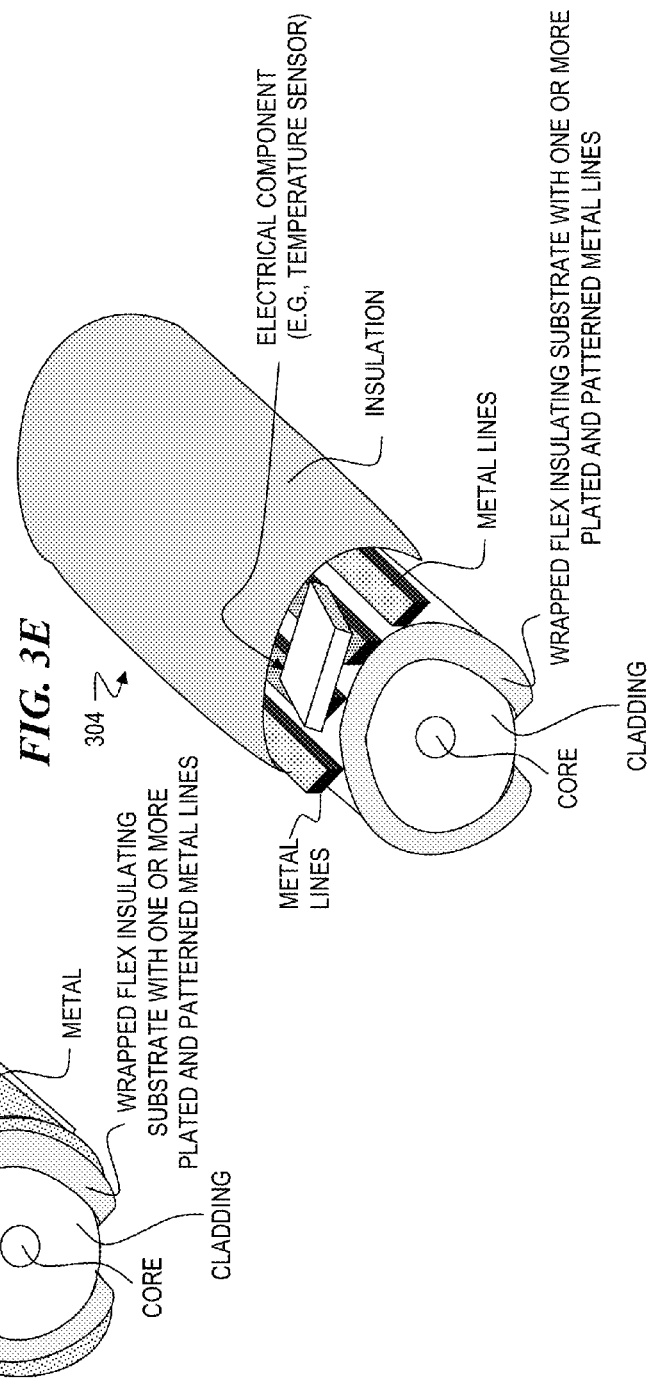
FIG. 3D
FIG. 3E

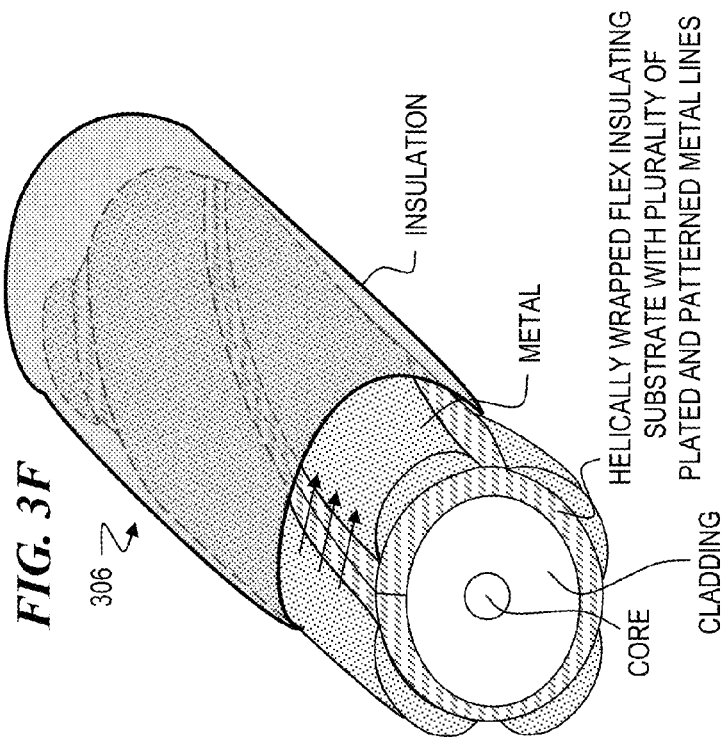

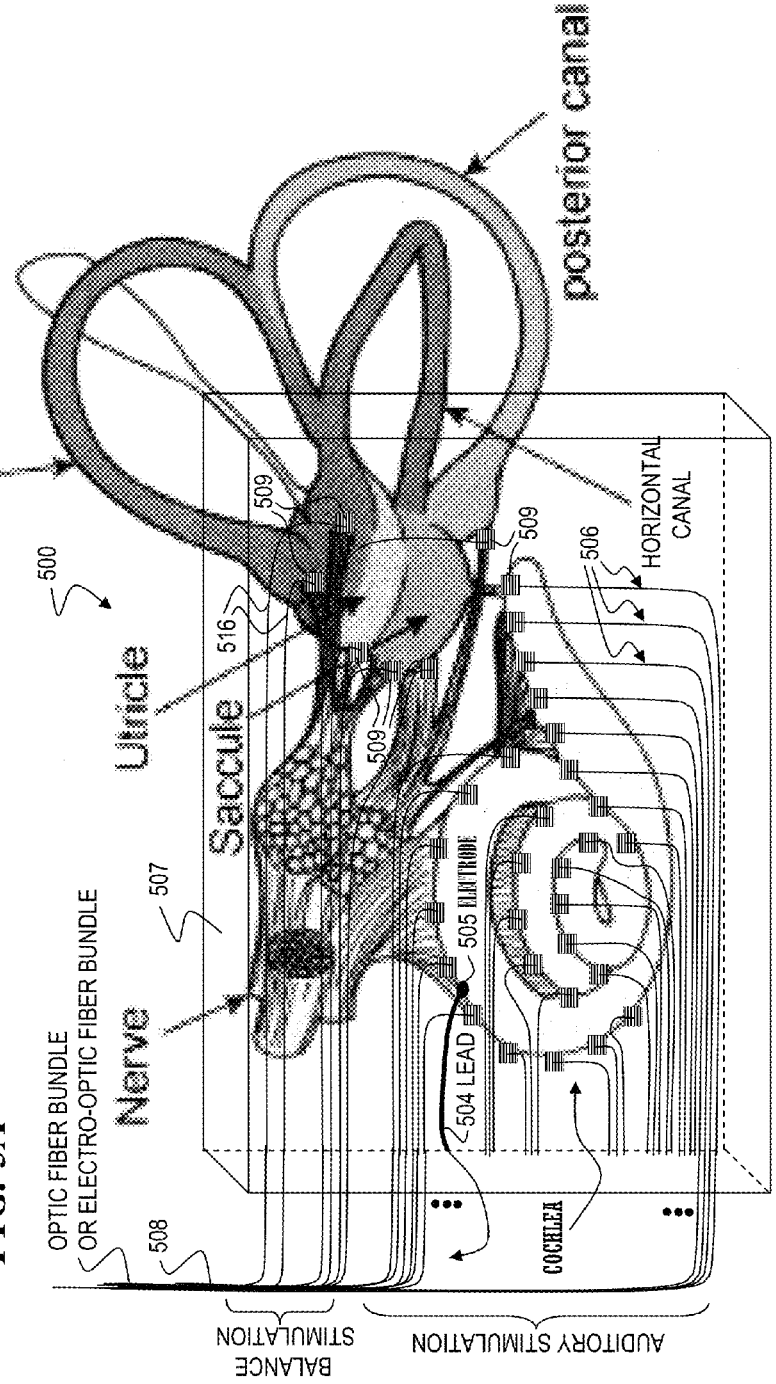
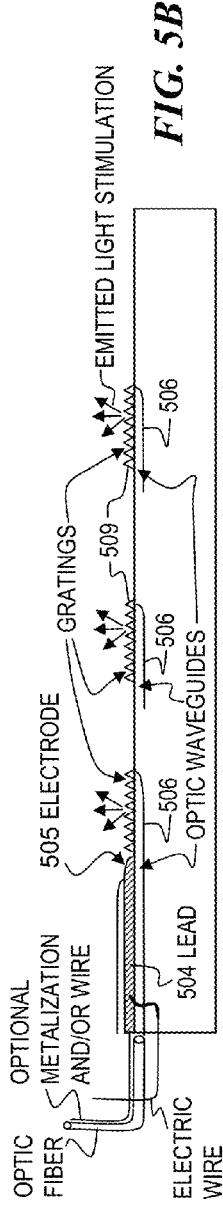
FIG. 5A
FIG. 5B

HYBRID OPTICAL-ELECTRICAL PROBES FOR STIMULATION OF NERVE OR OTHER ANIMAL TISSUE

CROSS-REFERENCE TO RELATED APPLICATIONS

This is a divisional of and claims benefit of U.S. patent application Ser. No. 13/022,576 filed Feb. 7, 2011 (which issued as U.S. Pat. No. 8,357,187 on Jan. 22, 2013), titled "HYBRID OPTICAL-ELECTRICAL PROBES FOR STIMULATION OF NERVE OR OTHER ANIMAL TISSUE," which claims benefit of U.S. patent application Ser. No. 12/018,185 filed Jan. 22, 2008 (which issued as U.S. Pat. No. 7,883,536 on Feb. 8, 2011), titled "HYBRID OPTICAL-ELECTRICAL PROBES," which claims benefit of U.S. Provisional Patent Application No. 60/885,879 filed Jan. 19, 2007, titled "Hybrid Optical-Electrical Probes"; and U.S. Provisional Patent Application No. 60/964,634 filed Aug. 13, 2007, titled "VCSEL Array Stimulator Apparatus and Method for Light Stimulation of Bodily Tissues";

each of which is incorporated herein by reference in its entirety.

This invention is also related to prior

U.S. patent application Ser. No. 11/257,793 filed Oct. 24, 2005 (which issued as U.S. Pat. No. 7,736,382 on Jun. 15, 2010), titled "Apparatus and Method for Optical Stimulation of Nerves and Other Animal Tissue";

U.S. patent application Ser. No. 11/536,639 filed Sep. 28, 2006 (which issued as U.S. Pat. No. 7,988,688 on Aug. 2, 2011), titled "Miniature Apparatus and Method for Optical Stimulation of Nerves and Other Animal Tissue";

U.S. patent application Ser. No. 11/536,642 filed Sep. 28, 2006, titled "Apparatus and Method for Stimulation of Nerves and Automated Control of Surgical Instruments";

U.S. Provisional Patent Application Ser. No. 60/872,930 filed Dec. 4, 2006, titled "Apparatus and Method for Characterizing Optical Sources Used with Human and Animal Tissues";

U.S. patent application Ser. No. 11/948,912 filed Nov. 30, 2007, titled "Apparatus and Method for Characterizing Optical Sources Used with Human and Animal Tissues";

U.S. Provisional Patent Application No. 60/884,619 filed Jan. 11, 2007, titled "Vestibular Implant Using Infrared Nerve Stimulation"; and U.S. patent application Ser. No. 11/971,874 filed Jan. 9, 2008 (which issued as U.S. Pat. No. 8,012,189 on Sep. 6, 2011), titled "Method and Vestibular Implant Using Optical Stimulation of Nerves";

each of which is incorporated herein by reference in its entirety.

FIELD OF THE INVENTION

The invention relates generally to tissue optics (interactions of light with human or animal tissue) combined with electrical-signal sensing and/or stimulation, and more particularly to methods and implantable apparatus for stimulating animal tissue in vivo, for example, nerves (e.g., nerves of the auditory system in animals; for example, some embodiments use an implantable device in medical treatments for auditory, balance, and dizziness conditions of the vestibular system using light, such as infrared wavelengths, for optical and/or electrical stimulation of nerves of the inner ear and related bodily systems), and utilizing electrical-signal sensing and/or stimulation.

BACKGROUND OF THE INVENTION

A person's inner ear includes the labyrinth, a delicate memberous system of fluid passages that includes both the cochlea (which is part of the auditory system), and the vestibular system (which provides part of the sense of balance). The eyes also provide signals used for balance, as do joint and muscle receptors and the cerebellum. The brain, specifically the vestibular nuclear complex, receives and analyzes the information from these systems, and generates signals that control a person's balance.

Each inner-ear includes three semicircular canals and a vestibule, the region where the semicircular canals converge, and which is close to the cochlea (the hearing organ). The vestibular system also works with the visual system to keep objects in focus when the head is moving.

Interference with, or infection, of the labyrinth can result in a syndrome of ailments called labyrinthitis. The symptoms of labyrinthitis include temporary nausea, disorientation, vertigo, and dizziness. Labyrinthitis can be caused by viral infections, bacterial infections, physical blockage of the inner ear, or due to decompression sickness.

Some people lose vestibular hair cells or suffer from balance and dizziness problems that are not readily treatable through therapy and/or drugs. These conditions can be very debilitating, since the affected person must remain still to minimize unpleasant dizziness or feeling continuously "seasick." The condition can also affect their ability to walk or keep their balance in general.

The semicircular canals in the inner ear form three loops that are fluid filled and sense rotation of a person.

Otoliths (earstones) are small particles composed of calcium carbonate supported in a gelatinous matrix in the viscous fluid of the saccule and utricle (the utricle is located in the vestibule, between the semicircular canals and the cochlea within a swelling adjacent to the semicircular canals, and the saccule is closer to the cochlea). The inertia of these small particles (sometimes referred to as stones or crystals) causes them to stimulate hair cells differently when the head moves. The hair cells send signals down sensory nerve fibers via the vestibulocochlear cranial nerve (CN VIII), which are interpreted by the brain as motion. The vestibular nucleus coordinates inputs from the muscles responsible for posture via the spinal cord, information on control, balance, and movements via the cerebellum, and head and neck movements via cranial nerves III, IV, and VI.

The saccule and utricle together make the otolith organs. They are sensitive to gravity and linear acceleration. Because of their orientation in the head, the utricle is sensitive to a change in horizontal movement, and the saccule gives information about vertical acceleration (such as when in an elevator). The otolith organs also provide information to the brain orientation of the head, such as being in a vertical position or prone position, or being face-up or face-down.

When the head is in a normal upright position, the otolith presses on the sensory hair cell receptors. This pushes the hair cell processes down and prevents them from moving side to side. However, when the head is tilted, the pull of gravity on statoconia shift the hair cell processes to the side, distorting them and sending a message to the central nervous system that the head is no longer level but now tilted. The motion sensation from the otoliths is involved in a large number of reflexes. Damage to the otoliths or their central connections can impair ocular and body stabilization.

U.S. Pat. No. 7,225,028 issued to Della Santina et al. on May 29, 2007, and titled "Dual Cochlear/Vestibular Stimulator with Control Signals Derived from Motion and Speech Signals", is incorporated herein by reference. Della Santina et al. describe a system for treating patients affected both by hearing loss and by balance disorders related to vestibular hypofunction and/or malfunction, which includes sensors of sound and head movement, processing circuitry, a power source, and an implantable electrical stimulator capable of stimulating areas of the cochlea and areas of the vestibular system.

U.S. Patent Application Publication Number US 2007/0261127 A1 filed Jul. 24, 2006 by Edward S. Boyden and Karl Deisseroth, titled "LIGHT-ACTIVATED CATION CHANNEL AND USES THEREOF"; U.S. Patent Application Publication Number US 2007/0054319 A1 filed Jul. 24, 2006 by Edward S. Boyden and Karl Deisseroth, titled "LIGHT-ACTIVATED CATION CHANNEL AND USES THEREOF" filed Jul. 24, 2006; and U.S. Patent Application Publication Number US 2007/0053996 A1 filed Jul. 24, 2006 by Edward S. Boyden and Karl Deisseroth, titled "LIGHT-ACTIVATED CATION CHANNEL AND USES THEREOF" are all incorporated herein by reference. These describe compositions and methods for light-activated cation channel proteins and their uses within cell membranes and subcellular regions. They describe proteins, nucleic acids, vectors and methods for genetically targeted expression of light-activated cation channels to specific cells or defined cell populations. In particular the description provides millisecond-timescale temporal control of cation channels using moderate light intensities in cells, cell lines, transgenic animals, and humans. The descriptions provide for optically generating electrical spikes in nerve cells and other excitable cells useful for driving neuronal networks, drug screening, and therapy.

U.S. Pat. No. 6,748,275 issued to Lattner et al. on Jun. 8, 2004, and titled "Vestibular Stimulation System and Method" (herein "Lattner et al. '275 patent"), is incorporated herein by reference. Lattner et al. '275 patent describes an apparatus and method in which the portions of the labyrinth associated with the labyrinthine sense and/or the nerves associated therewith are stimulated to perform at least one of the following functions: augment or control a patient's respiratory function, open the patient's airway, induce sleep, and/or counteract vertigo.

U.S. Pat. No. 7,004,645 issued to Lemoff et al. on Feb. 28, 2006, and titled "VCSEL array configuration for a parallel WDM transmitter", is incorporated herein by reference. Lemoff et al. describe VCSEL array configurations. WDM is wavelength-division multiplexing. Transmitters that use several wavelengths of VCSELs are built up out of multiple die (e.g., ones having two-dimensional single-wavelength monolithic VCSEL arrays) to avoid the difficulty of manufacturing monolithic arrays of VCSELs with different optical wavelengths. VCSEL configurations are laid out to insure that VCSELs of different wavelengths that destined for the same waveguide are close together.

U.S. Pat. No. 7,116,886 issued to Colgan et al. on Oct. 3, 2006, and titled "Devices and methods for side-coupling optical fibers to optoelectronic components", is incorporated herein by reference. Colgan et al. describe optical devices and methods for mounting optical fibers and for side-coupling light between optical fibers and VCSEL arrays using a modified silicon V-groove, or silicon V-groove array, wherein V-grooves, which are designed for precisely aligning/spacing optical fibers, are "recessed" below the surface of the silicon. Optical fibers can be recessed below the surface of the silicon substrate such that a precisely controlled portion of the cladding layer extending above the silicon surface can be removed (lapped). With the cladding layer removed, the separation between the fiber core(s) and optoelectronic device(s) can be reduced resulting in improved optical coupling when the optical fiber silicon array is connected to, e.g., a VCSEL array.

U.S. Pat. No. 7,031,363 issued to Biard et al. on Apr. 18, 2006, and titled "Long wavelength VCSEL device processing", is incorporated herein by reference. Biard et al. describe a process for making a laser structure such as a vertical cavity surface emitting laser (VCSEL). The VCSEL designs described include those applicable to the 1200 to 1800 nm wavelength range U.S. Pat. No. 6,546,291 issued to Merfeld et al. on Apr. 8, 2003, and titled "Balance Prosthesis", is incorporated herein by reference. Merfeld et al. describe a wearable balance prosthesis that provides information indicative of a wearer's spatial orientation. The balance prosthesis includes a motion-sensing system to be worn by the wearer and a signal processor in communication with the motion-sensing system. The signal processor provides an orientation signal to an encoder. The encoder generates a feedback signal on the basis of the estimate of the spatial orientation provides that signal to a stimulator coupled to the wearer's nervous system.

Vestibular problems in the inner ear, the semicircular canal organs or the otolith organs can cause very debilitating conditions, including dizziness and vertigo. Improved apparatus and methods are needed to diagnose and/or treat various problems in animals, including vestibular problems.

BRIEF SUMMARY OF THE INVENTION

The present invention includes combination probes having both optical transmission and electrical transmission capabilities. In some embodiments, an optical fiber having one or more optical waveguides (e.g., fibers having cores defined by increased index of refraction (as are typical of conventional optical fibers and light-transmission fibers) or photonic-crystal structures, both of which are described in the commonly assigned U.S. patent application Ser. No. 11/420,729 titled "FIBER- OR ROD-BASED OPTICAL SOURCE FEATURING A LARGE-CORE, RARE-EARTH-DOPED PHOTONIC-CRYSTAL DEVICE FOR GENERATION OF HIGH-POWER PULSED RADIATION AND METHOD" filed May 26, 2006 (which issued as U.S. Pat. No. 7,391,561 on Jun. 24, 2008) by Fabio Di Teodoro et al., which is incorporated herein by reference). In some embodiments, the optical fiber is at least partly covered with or connected along an electrical conductor (such as a metal film or wire).

In some embodiments, the probe is attached to an implanted device (such as a battery-powered microprocessor-controlled device that transmits an optical signal to stimulate a portion of an animal (such as the vestibular nerves of a human, for example; however, the invention is not limited to the vestibular system, but rather is generally useful for any use that benefits from both optical and electrical signals to and from one or more tissues of an animal) and that electrically senses a biological response (such as a compound nerve-action potential (CNAP) response of a stimulated nerve)) or a physical condition (such as the temperature at the probe end, in order to determine the amount of heating resulting from the optical stimulation, so as to deliver an amount of light that is effective to obtain the nerve stimulation response without overheating and damaging tissue). In some embodiments, the sensed response or condition is used to control (e.g., increase, decrease, start, or stop) the optical signal in order to obtain better treatment effectiveness and more precise control of the desired response. In some embodiments, the optical fiber is also or instead used to deliver a much more intense light pulse or series of pulses, in order to provide therapy-type or surgery-type results, such as ablating unwanted tissue, wherein there is an interaction between the intense light pulses that is sensed by received electrical signals conducted from the fiber tip along the electrical conductors on the optical fiber, and/or enhanced by electrical signals that are delivered to the fiber tip along the electrical conductors on the optical fiber.

In other embodiments, the probe of the present invention is used for intraoperative monitoring to both stimulate and detect nerve signals of nerves that are desired to be retained during surgery to remove other tissue. As discussed by Yamakami et al. in "Intraoperative monitoring of cochlear nerve compound action potential in cerebellopontine angle tumour removal", *Journal of Clinical Neuroscience*, ISSN 0967-5868, 2003, vol. 10, no. 5, pp. 567-570 (which is incorporated herein by reference), because of technical difficulty, CNAP monitoring has not been popular during operations such as for the removal of cerebellopontine angle (CPA) tumour. To clarify the efficiency of intraoperative CNAP monitoring, Yamakami et al. designed an intracranial electrode for CNAP monitoring and performed the simultaneous monitoring of CNAP and auditory brainstem response (ABR) in patients undergoing CPA tumor removal in an attempt to preserve hearing. The present invention provides an improved probe that can be used in such situations (e.g., not using an implanted device, but rather using one or more external optical sources and one or more electrical detectors, wherein a single probe can both optically stimulate the nerve in one or more places, and detect CNAP responses in one or more places.

In some embodiments, the probes of the present invention are used with a nerve stimulator, such as described in U.S. Provisional Patent Application No. 60/872,930 filed Dec. 4, 2006, but in other embodiments, could be used for other applications as well (such as laser surgery where the optical fiber is used to deliver the laser pulses for the surgical procedure). Nominally, the probe of the present invention stimulates the nerve optically and the CNAP that results from the optical stimulation of the nerve is detected electrically. In other embodiments, other physiological effects are detected electrically beforehand that tell the optical stimulator when to fire (i.e., transmit an optical stimulation signal). In yet other embodiments, the device of the present invention works by electrically stimulating the nerve and detecting its response optically.

In some embodiments, the device of the present invention is used in the stimulation of the vestibular system. It is often necessary, during the placement of probes (e.g., optical fibers), to be able to both stimulate and detect the response resulting from the stimulation of the vestibular system. Being able to have a single probe that does this facilitates this placement process.

Accordingly, some embodiments of the present invention provide an apparatus that includes one or more operative optical fibers and one or more operative electrical conductors in a single small-diameter cable. In some embodiments, the electrical conductors are thin-film structures that are vacuum deposited, evaporated, plated, sputtered or otherwise formed as a film (such as a metal-film structure having one or more metal layers (e.g., an adhesion layer (such a nickel, cobalt, copper, vanadium or the like) covered by a conduction, shielding, and/or protective layer (such as nickel, gold, platinum or the like)) directly on the optical fiber. In some embodiments, a plurality of electrically conducting layers are deposited as coaxial films separated from one another by electrically insulating layers (such as glass, polymer, ceramic, or the like), such that, in some embodiments, the outer conductive layer(s) forms an electromagnetic shield for the signals carried on the inner conductive layer(s). In some embodiments, the electrical conductors are formed as separated conductors each located at different angles around the optical fiber (in some such embodiments, a metal-film structure is deposited to completely cover or substantially cover the length and circumference of the optical fiber, and then lengthwise channels are removed (e.g., etched, milled, ablated, or the like) to leave lengthwise conductors on the outside of the fiber. In some embodiments, the resulting fiber from any of the above fabrication processes is covered by one or more protective and/or strengthening layers (which may be electrically conductive or insulating, depending on the application and requirements of the system).

In other embodiments, the electrical conductors are formed as preformed structures (such as individual wires, sets of side-by-side wires, or coaxial wires), and then connected to the optical fiber by helical winding, adhesive, enclosing by a jacket, and/or other methods.

Although the use of the present invention is described for a few specific applications such as stimulation and sensing of the vestibular system, in other embodiments, the present invention provides both electrical and optical signals transmitted on a combination fiber to one or more of a wide variety of body locations and tissue types. In various embodiments, the combination fiber includes one or more optical waveguides (whether as one or more cores in a single optical fiber or one or more optical fibers each having one or more cores, wherein if a plurality of cores are used, in some embodiments, the fibers are adhesively connected to one another, fused to one another, and/or held together within a cannula or sheath). In some embodiments, a plurality of combination fibers are used, either all going from a common source to a common destination, or going from a plurality of sources to a single destination or from a single source to a plurality of destinations.

In other embodiments, the present invention provides an optical-electrical slab or substrate having an integrated electro-optical circuit (IEOC) of both electrical components (such as sensor and/or stimulation electrodes that are placed against a tissue) and optical components (such as waveguides for routing and delivering light, diffraction gratings (for getting light to leave the IEOC towards a tissue, or for receiving optical signals (whether infrared (IR), visible, or ultraviolet (UV)) from a tissue). In some such embodiments, the optical-electrical slab is operatively connected to an optical-electrical fiber assembly, wherein the optical-electrical slab forms a functional interface to the tissue of a living animal (such as a human), and the optical-electrical fiber assembly provides the signal and/or power connections to and from the optical-electrical slab. For example, in some embodiments, the optical-electrical slab is the interface to the cochlea of a patient's ear and/or vestibular system, and the optical-electrical fiber assembly connects between the cochlear optical-electrical slab and an implanted or external controller that provides optical and/or electrical signals through the optical-electrical fiber assembly between the controller and the cochlear optical-electrical slab. In other embodiments, the optical-electrical slab is used as the functional interface to another tissue of the patient.

In some embodiments, the present invention is used in applications where there is a need for precise placement of an electrode, but with the requirement to stimulate a large number of nerves, either simultaneously or individually. A single-core optical element (e.g., a fiber with a single waveguide) allows for extremely precise stimulation but can lack the ability to supply and/or spread enough power to stimulate large areas of nerves. In some embodiments, the electrical portion of the probe lacks specificity (since even with a point source of electricity, the electrical signal will spread across electrically conductive tissue), but can provide sufficient power to stimulate large areas. In some embodiments, the optical-electrical probe of the present invention is used in deep brain stimulation where locating the probe at the interface between the thalamus and hypothalamus is important, but once there, a relatively large area of the brain needs to be stimulated.

The present invention provides an architecture that exploits one of the biggest advantages of optical stimulation, namely, it does not create optical crosstalk. Therefore stimulation and detection can occur in close proximity; a technique not currently practical using all-electrical approaches.

The present invention provides several approaches to doing this. One uses discrete electrical probes located immediately adjacent to the optical fiber. The fiber and electrodes can be held together in a cannula, glass tube, polyimide sleeve or any other biocompatible material. This has the advantage of being very simple to do and allows independent optimization of the optical fiber and electrical probes.

A more compact approach, used in some embodiments, actually uses the fiber to carry both the optical and electrical signals. It is well known how to put metallized coatings on optical fibers. It is done routinely in order to be able to attach the fiber to optical mounts using solder for the purpose of alignment. In some embodiments, the metal-layer structure includes typically a combination of Ni (for adhesion to the fiber), Pt, and/or Au (for wetability to the solder). In the present invention, the Au layer provides an excellent conductor for the electrical signal. Several configurations of the conductor(s) on an optical fiber are shown in the attached figures. The simplest monopolar configuration will be adequate for many applications. However, the multi-electrode configurations can provide additional functionality as well as spatial selectivity.

Other embodiments use a configuration where the fiber is slid into a sleeve or jacket (or wrapped with a spirally wound film having one or more length-wise metallized conductors that when wound forms such a sleeve) that is patterned with the electrodes (e.g., a Kapton or other flex circuit, wherein metal conductors are formed and patterned (e.g., as parallel conductors extending along its length) on a polymer substrate (and optionally covered with another polymer, glass, silicon nitride or the like as a top insulator), and this substrate with its conductors is wound or wrapped on the optical fiber). This allows independent fabrication of more complex electrode patterns without having to develop new processes for metallizing the fibers. The Kapton-substrate circuits also readily lend themselves to easy termination. Any flexible substrate that can support a metal pattern and is biocompatible can be used for this configuration.

BRIEF DESCRIPTION OF THE DRAWINGS

FIG. 1A shows a perspective view of an optical fiber 101 having a single co-axial metal electrical conductor deposited on the optical fiber.

FIG. 1B shows a perspective view of an optical fiber 102 having a split (called two-part, two-conductor, or bipolar) co-axial metal electrical conductor deposited on the optical fiber.

FIG. 1C shows a cross-section view of an optical fiber 101 having a single co-axial metal electrical conductor (monopolar) deposited on the optical fiber.

FIG. 1D shows a cross-section view of an optical fiber 102 having a split two-part/bipolar co-axial metal electrical conductor deposited on the optical fiber.

FIG. 1E shows a cross-section view of an optical fiber 103 having a split three-part/tripolar co-axial metal electrical conductor deposited on the optical fiber.

FIG. 1F shows a cross-section view of an optical fiber 104 having a split four-part/dual-bipolar co-axial metal electrical conductor deposited on the optical fiber.

FIG. 2A is a perspective view of an embodiment of the invention in which metallic coating of an optical fiber functions in an electrode capacity, in a bipolar configuration with the electrodes offset, relative to one another, in the Z direction.

FIG. 2B is a perspective view of an embodiment of the invention in which coaxial metallic coatings of an optical fiber functions in an electrode capacity, in a bipolar configuration with the electrodes offset, relative to one another, in the Z direction.

FIG. 2C is a perspective view of an embodiment of the invention in which coaxial metallic coatings of an optical fiber functions in an electrode capacity, in a bipolar configuration with the electrodes offset, relative to one another, in the Z direction, and in which the coaxial film outer conductive layer forms an electromagnetic shield for the signals carried on the inner conductive coatings.

FIG. 2D shows a cross-section view of an optical fiber having a split two-part/bipolar co-axial metal electrical conductor deposited on the optical fiber and a coaxial film outer conductive layer deposited on an insulator that covers the two-part electrical conductor.

FIG. 3A is a perspective view of an embodiment of the invention in which an optical fiber is co-located with a separate, monopolar electrode, within a sheathing or a cannula.

FIG. 3B is a perspective view of an embodiment of the invention in which an optical fiber is co-located with a separate, bipolar electrode.

FIG. 3D is a perspective view of an embodiment of the invention in which an optical fiber is wrapped with a flex circuit that has been patterned with one or more electrical lines.

FIG. 3E is a perspective view of an embodiment of the invention in which an optical fiber is wrapped with a flex circuit that has been patterned with one or more electrical lines.

FIG. 3F is a perspective view of an electro-optic fiber embodiment 306 of the invention in which an optical fiber is wrapped in a helical winding pattern with a flex circuit that has been patterned with one or more electrical lines.

FIG. 5A is a diagram of an implanted device, with an optical-fiber/electrode leads connected to a planar substrate for interfacing to the cochlea and/or the vestibular organs.

FIG. 5B is a cross-section diagram of implanted device 500, with an optical-fiber/electrode leads connected to a planar substrate to the cochlea and/or the vestibular organs.

DETAILED DESCRIPTION OF THE INVENTION

Figure 3C:
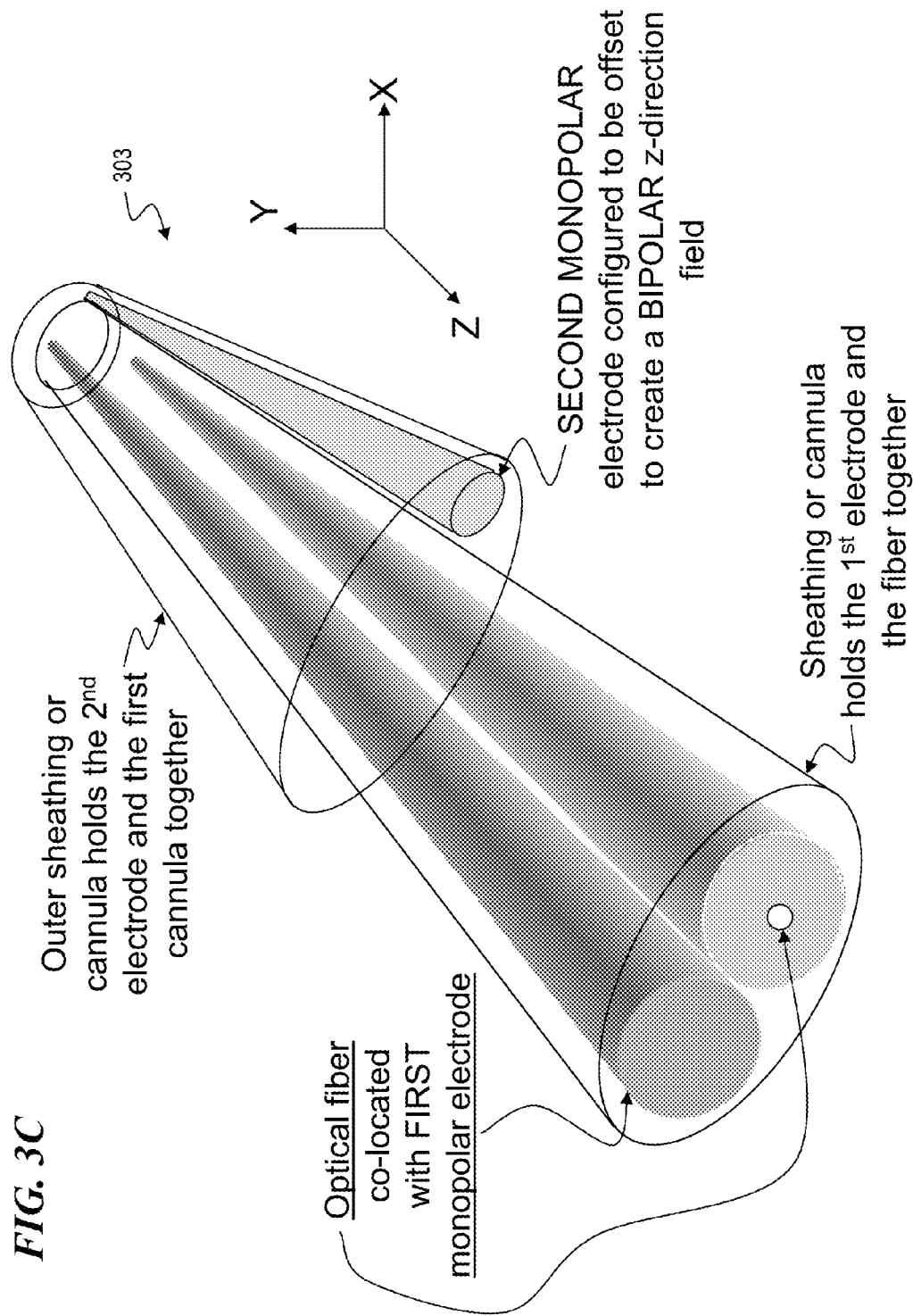
FIG. 3C is a perspective view of an embodiment of the invention in which an optical fiber is co-located with a separate, bipolar electrode, with elements of the latter offset in the Z direction, relative to one another.

Although the following detailed description contains many specifics for the purpose of illustration, a person of ordinary skill in the art will appreciate that many variations and alterations to the following details are within the scope of the invention. Accordingly, the following preferred embodiments of the invention is set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component that appears in multiple figures. Signals and connections may be referred to by the same reference number or label, and the actual meaning will be clear from its use in the context of the description.

As used herein, an optical-waveguide device is defined as any device that provides a constrained guided optical path in a solid, for example, an optical fiber having one or more waveguide cores or an optical slab or monolithic substrate having a width and length each larger than the thickness, and having one or more waveguides formed therein (e.g., laterally spaced waveguides formed by diffusion of a index-modifying material through a mask to form surface or near-surface waveguides). An optical fiber is defined as any device having one or more cores or internal waveguides and a length much longer than a transverse width, for example a glass fiber drawn from a melt or preform or extruded from an extruder. A thin optical fiber is defined as a fiber that is thin enough to be readily bent to some non-infinite radius (e.g., a conventional optical fiber). A rod-like fiber (also referred to hereafter as "rod waveguide" or simply "rod") is defined as a fiber that is thick enough to readily hold its shape when released (e.g., a glass rod having a diameter of 1 millimeter (mm) or more). An optical ribbon is defined as a fiber having two or more signal cores laterally spaced across a width of the fiber. An optical ribbon rod is defined as a fiber having two or more signal cores laterally spaced across a width of the fiber and that is thick enough to readily hold its shape when released.

In some embodiments, the present invention provides a combined optical fiber and electrical conductor that is configured to deliver optical stimulation to animal tissue (such as nerves of humans, and in particular, in some embodiments, to one or more of the vestibular nerves of the inner ear in order to improve balance and/or reduce dizziness) and to deliver and/or receive electrical signals to and/or from the nerves adjacent to the optical fiber. In some embodiments, one or more metal films are applied to an optical fiber. In some embodiments, the electrical films are applied and/or etched to create two or more films around the optical fiber and separated tangentially from one another by longitudinal gaps that this provide longitudinal conductors along a length of the fiber. In some embodiments, these conductors spiral around the fiber, to create twisted pairs of conductors (or twisted conductors in multiples other than two) in order to reduce pickup of electromagnetic interference (EMI). In some embodiments, the conductors include a co-axial shield layer (e.g., a metal film deposited outside an insulator layer that covers inner electrical conductors). In some embodiments, conductors other than metal are used. In some embodiments, the conductors include one or more wires wound around the optical fiber. In some embodiments, one or more separate conductors (such as wire) are encased with one or more optical fibers in an insulated and/or conductive jacket that provides physical protection and/or electrical shielding. In some embodiments, the jacket is formed by winding a film in a spiral around one or more optical fibers and/or one or more conductors (such as films deposited on the optical fibers and/or wires).

FIG. 1A shows a perspective view of an optical fiber 101 having a single co-axial metal electrical conductor deposited on the optical fiber. FIG. 1B shows a perspective view of an optical fiber 102 having a split (called two-part, two-conductor, or bipolar) co-axial metal electrical conductor deposited on the optical fiber. FIG. 1C shows a cross-section view of an optical fiber 101 having a single co-axial metal electrical conductor (monopolar) deposited on the optical fiber. FIG. 1D shows a cross-section view of an optical fiber 102 having a split two-part/bipolar co-axial metal electrical conductor deposited on the optical fiber. FIG. 1E shows a cross-section view of an optical fiber 103 having a split three-part/tripolar co-axial metal electrical conductor deposited on the optical fiber. FIG. 1F shows a cross-section view of an optical fiber 104 having a split four-part/dual-bipolar co-axial metal electrical conductor deposited on the optical fiber.

Embodiments of the invention are shown in which metallic coating of an optical fiber functions in an electrode capacity in a monopolar configuration 101 (i.e., an optical fiber in conjunction with a single electrical conductor), a bipolar configuration 102 (i.e., an optical fiber in conjunction with two electrical conductors), a tripolar configuration 103 (i.e., an optical fiber in conjunction with three electrical conductors, for example a power, a ground, and a signal conductor, or a positive power, ground, and negative power, or a differential signal and a ground), and a dual-bipolar configuration 104. Light that is emitted from the optical fiber in any of these embodiments may stimulate neural tissue, with chemical-electrical activity (thought to be caused, in some embodiments, by the near-instantaneous temperature change caused by the optical signal heating the tissue) of the stimulated neural tissue creating, in some embodiments, an electrical field that will result in an electrical signal being transmitted back along the electrode component of the optical-fiber/electrode assembly (or lead)—an electrical signal that is proportional to the electrical field created by the tissue's response to the light stimulation.

Optical fibers can be very small in diameter, which is advantageous in allowing relatively unobtrusive insertion into delicate and densely packed neural areas. A further advantage of optical fibers—even small-diameter optical fibers—is a certain inherent stiffness that assists in their insertion deep into biological tissue. Micro-filament electrical wires typically lack such stiffness. The present invention's joining together delicate electrical-field-sensing electrodes with optical fibers that have a certain inherent stiffness, permits the optical-fiber/electrode lead to be inserted to remotely located areas to stimulate biological tissue with light, and to electrically measure the response of the target tissue to that light stimulation.

FIG. 2A shows a perspective view of an embodiment of the invention in which metallic coating of an optical fiber functions in an electrode capacity, in a bipolar configuration with the electrodes offset, relative to one another, in the Z direction.

FIG. 2B is a perspective view of an embodiment of the invention in which coaxial metallic coatings of an optical fiber functions in an electrode capacity, in a bipolar configuration with the electrodes offset, relative to one another, in the Z direction.

FIG. 2C is a perspective view of an embodiment 202 of the invention in which coaxial metallic coatings of an optical fiber functions in an electrode capacity, in a bipolar configuration with the electrodes offset, relative to one another, in the Z direction, and in which a coaxial film outer conductive layer forms an electromagnetic shield for the signals carried on the inner conductive layers.

FIG. 2D shows a cross-section view of an optical fiber 203 having a split two-part/bipolar co-axial metal electrical conductor deposited on the optical fiber and a coaxial film outer conductive layer shield deposited on an insulator that covers the two-part electrical conductor.

FIG. 3A shows a perspective view of an embodiment 301 of the invention in which an optical fiber is co-located with a separate, monopolar electrode, within a sheathing or a cannula.

FIG. 3B shows a perspective view of an embodiment 302 of the invention in which an optical fiber is co-located with a separate, bipolar electrode.

FIG. 3C shows a perspective view of an embodiment 303 of the invention in which an optical fiber is co-located with a separate, bipolar electrode, with elements of the latter offset in the Z direction, relative to one another.

FIG. 3D is a perspective view of an electro-optic fiber embodiment 305 of the invention in which an optical fiber is wrapped (e.g., in some embodiments, a helical winding pattern is used, wherein the metal lines are in a helical pattern simulating a twisted pair) with a flex circuit that has been patterned with one or more electrical lines (two in this example). In some embodiments, the flex substrate is a suitable polymer such as Kapton, and has one or more plated and patterned metal lines. In some such embodiments, the metal lines are exposed at the end of the fiber to form an electrical-field sensor, which is used, in some embodiments, as an electrical sensor to detect nerve action potentials, such as may be generated by optical stimulation delivered by the optical fiber.

FIG. 3E is a perspective view of an electro-optic fiber 304 embodiment of the invention in which an optical fiber is wrapped (e.g., in some embodiments, a helical winding pattern is used, wherein the metal lines are in a helical pattern simulating two twisted pairs) with a flex circuit that has been patterned with one or more electrical lines (four in this example). In some embodiments, the flex substrate is a suitable polymer such as Kapton™, and has one or more plated and patterned metal lines. In some such embodiments, the metal lines are connected to an electrical component (such as an amplifier to pre-amplify detected electrical signals at the end of the fiber to form an electrical-field sensor), which is used, in some embodiments, as an electrical sensor to detect nerve action potentials, such as may be generated by optical stimulation delivered by the optical fiber. In other embodiments, the electrical component is a temperature sensor used to detect the amount of heat generated by the optical nerve stimulation, in order to control the stimulation and prevent tissue damage that might otherwise be caused by accidental overheating. In some embodiments, a closed-loop system is formed, wherein the temperature sensor sends a temperature signal, and the electrodes on other metal lines send an electrical signal representing the nerve action potentials, wherein these signals control the optical stimulation signal that is sent (e.g., enough optical signal to trigger the CNAP but not so much as would cause undue heating of the tissue).

FIG. 3F is a perspective view of an electro-optic fiber embodiment 306 of the invention in which an optical fiber is wrapped in a helical winding pattern with a flex circuit that has been patterned with one or more electrical lines (four in this example), wherein the metal lines are in a helical pattern.

Figure 4A:
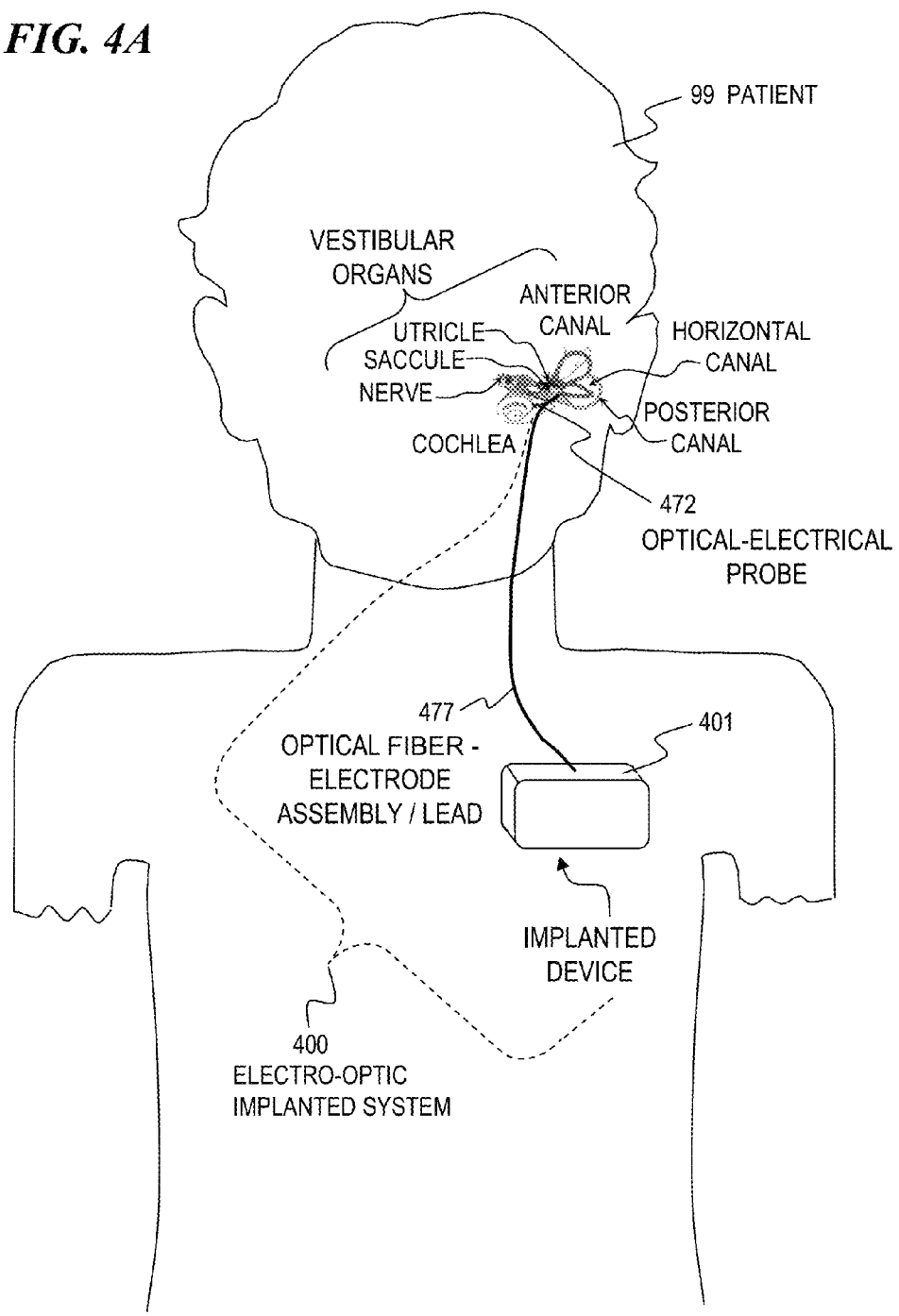
FIG. 4A is a diagram of an electro-optic implanted system 400 that includes an implanted device 401, with an optical-fiber/electrode lead 477 passing from the implanted device 401 to an optical-electrical probe 472 located at the vestibular organs.
Figure 4B:
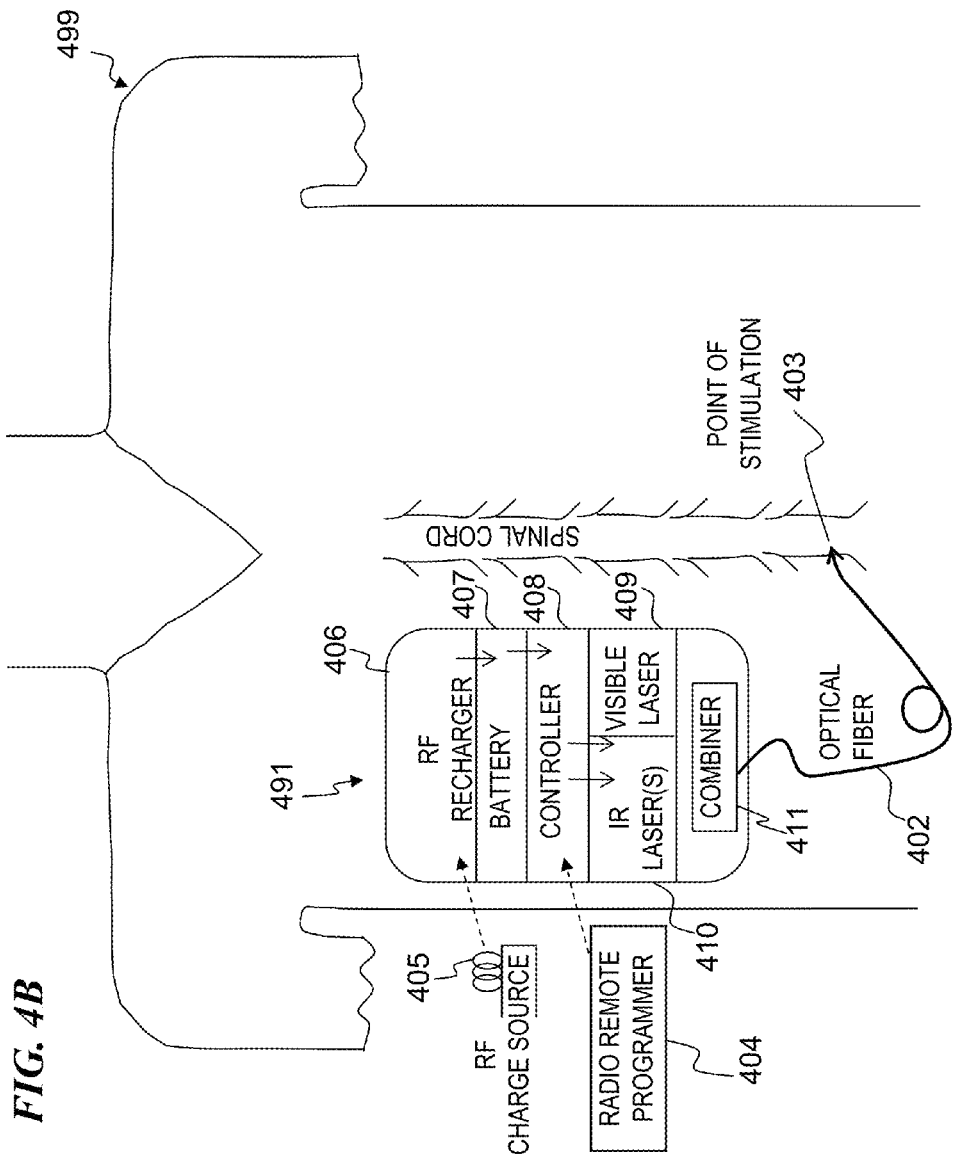
FIG. 4B is a schematic diagram of an implanted system 499 that includes an implanted nerve-stimulation device 491 having an IR laser 410.

FIG. 4B is a schematic 499 detailing an implantable version of the device that is powered and controlled via an external source. In some embodiments, an optical stimulator 491 is implanted into a subject (e.g., a patient) to provide an efficacious amount of IR-light stimulation to a nerve fiber. In some embodiments, this optical stimulator 491 contains components including an RF recharger 406, battery 407, controller 408, visible-laser source 409, IR-laser source 410 and combiner 411, with each being operatively coupled to each other such that the RF recharger 406 provides electrical power to the battery 407, which, in turn powers the controller 408. The controller 408 provides electrical power and control signals to the visible-laser source 409 and IR-laser source 410, regulating type and intensity of pulse generated by each of these sources. In some embodiments, the light from these sources (i.e., 409 and 410) is sent to a combiner 411 where the light is combined into a single beam. In some embodiments, the combiner 411 is operatively coupled to an optical-fiber structure 402 that is then positioned such that it can deliver an efficacious amount of IR light to a point of stimulation 403. In some embodiments, this point may be nerve fibers located along the spinal cord, whereas in other embodiments this point of stimulation 403 may be some other group of nerve fibers. As with other embodiments, light from the visible-laser source 409 is used to position the optical-fiber structure 402 relative to a point of stimulation 403. Once the optical-fiber structure 402 is positioned, IR laser light may be applied.

In at least one embodiment, control of the optical stimulator 491 is via a radio remote programmer 404 that sends control signals to the above-described controller 408. In some embodiments, an RF charge source 405 is used to supply electrical power to the optical stimulator 491.

FIG. 4A shows a diagram of an electro-optic implanted system 400 that includes an implanted device 401, with an optical-fiber/electrode lead 477 passing from the implanted device 401 to an optical-electrical probe 472 located at the vestibular organs.

FIG. 5A is a perspective diagram of an implanted device 500, with an optical-fiber/electrode leads connected to a planar substrate to the cochlea and/or the vestibular organs. In some embodiments, device 500 includes an integrated optical substrate 507 that, in some embodiments, is connected to a plurality of optic fibers 508. In some embodiments, integrated optical substrate 507 includes a plurality of optical waveguides 506, each leading to one or more Bragg gratings 509 (in some embodiments, each grating 509 is situated to emit light at a different location along the cochlea and/or its nerves, in order to stimulate (using optical signals) different frequencies (by the location on the cochlea) and different loudnesses (by the pulse repetition rate) using light delivered by different waveguides to the various locations. In some embodiments, a high-density grid of gratings and/or other waveguide endings are located across the substrate 507 (e.g., in a Cartesian grid), such that the appropriate grid locations to deliver the desired optical signals can be determined empirically after the device is implanted, such that the desired auditory nerves are properly stimulated to restore or create a hearing sensation. In some embodiments, integrated optical substrate 507 also includes one or more electrical electrodes 505 that are deposited on integrated optical substrate 507 using conventional integrated-circuit techniques using suitable metals such as described as coating the fiber optics. In some embodiments, these electrodes 505 are used to sense a response to the optical stimulation. In other embodiments, these electrodes 505 are used to deliver electrical stimulation signals (e.g., from implanted device 400).

In some embodiments, the plurality of optical waveguides includes waveguides 516 and gratings 509 that are placed to stimulate the vestibular system (the nerves of the three semicircular canals and/or the two otolith organs) to treat dizziness and or balance problems.

In some embodiments, the bundle of optical fibers 508 are connected to the optical waveguides 506, and the waveguides 506 are formed, using techniques such as, for example, are described in U.S. Pat. Nos. 6,493,476, 6,626,678, 6,690,873, and 6,330,388 by Mark Bendett et al., which are incorporated herein by reference.

FIG. 5B is a cross-section diagram of implanted device 500, with an optical-fiber/electrode leads connected to a planar substrate to the cochlea and/or the vestibular organs. Gratings 509 form the termination and emitting points for optical waveguides 506, and electrodes 505 form the electrical termination for electrical leads 504. In some embodiments, the optical waveguides are used for either stimulation, sensing, or both. In some embodiments, the electrodes are used for either stimulation, sensing, or both. These, in various embodiments, can be used for any tissue stimulation or sensing in the body.

By using a vestibular implant to achieve infrared nerve stimulation, the vestibular function can be restored to improve balance and/or avoid dizziness. The infrared nerve-stimulation technique is significant since it can selectively stimulate certain vestibular nerves without simultaneously spreading the stimulation to other sets of vestibular nerves or other nerves such as the cochlear nerve. In some embodiments, the device has as few as five (5) channels to control the three (3) rotational Vestibular sensors (i.e., nerves of the semicircular canals) and the two (2) linear vestibular sensors (i.e., nerves of the otolith organs—the utricle and saccule, where the utricle is located in the vestibule, between the semicircular canals and the cochlea within a swelling adjacent to the semicircular canals, and the saccule is closer to the cochlea). In addition, in some embodiments, the technique of varying the wavelength is used to control the penetration depth of the nerve stimulator, which is used to externally stimulate the vestibular organs without having to penetrate the organs. This is extremely beneficial since it would be a less invasive surgery and the implantable device is held within the patient's body, which thus reduces the risk of infections and other complications.

In some embodiments, the present invention provides a multi-core fiber or multiple individual fibers, wherein each core or each fiber is connected to transmit a different optical signal (e.g., the cores or fibers, in some embodiments, end at different points along the fiber), such that the different optical signals stimulate different points of the vestibular system. Similarly, in some embodiments, different electrical conductors are exposed at different points along the fiber, in order to detect CNAP or other signals from different points along a nerve, or from different nerves.

The invention provides an optical-signal vestibular-nerve stimulation device and method that provides different nerve stimulation signals to a plurality of different vestibular nerves, including at least some of the three semicircular canal nerves and the two otolith organ nerves. In some embodiments, balance conditions of the person are sensed by the implanted device, and based on the sensed balance conditions, varying IR nerve-stimulation signals are sent to a plurality of the different vestibular nerves.

In some embodiments, the present invention provides a method that includes obtaining light from an optical source; and transmitting the light to respective nerves of each of a plurality of inner-ear balance organs of an animal.

In some embodiments, the transmitting includes transmitting different amounts of the light through optical fibers to stimulate respective nerves of each of the plurality of inner-ear balance organs.

In some embodiments, the transmitting includes transmitting different wavelengths of the light to stimulate respective nerves of each of the plurality of inner-ear balance organs.

In some embodiments, the obtaining light includes implanting a self-contained IR laser device.

In some embodiments, the obtaining light includes implanting a self-contained battery-powered device.

In some embodiments, the animal is a human person. Some embodiments further include sensing a condition that affects balance, and wherein the transmitting includes transmitting different light signals to each of a plurality of different balance-sense organs to provide the person sense-of-balance nerve stimulation.

In other embodiments, the present invention provides an apparatus that includes an optical source; and a transmission medium configured to transmit light from the optical source to respective nerves of each of a plurality of inner-ear balance organs of an animal.

In some embodiments, the transmission medium includes a plurality of optical fibers, and the optical source couples different amounts of the light through the plurality of optical fibers to stimulate different respective nerves of each of the plurality of inner-ear balance organs.

In some embodiments, the optical source couples different wavelengths of the light to stimulate different respective nerves of each of the plurality of inner-ear balance organs.

In some embodiments, the optical source includes a self-contained implantable IR laser device.

In some embodiments, the optical source includes a self-contained battery-powered device.

In some embodiments, the animal is a human person. Some embodiments further include at least one sensor configured to sense a condition that affects balance, and wherein the transmission medium transmits different light signals, based on the sensed condition, to each of a plurality of different balance-sense organs to provide the person sense-of-balance nerve stimulation.

In other embodiments, the present invention provides an apparatus that includes means for obtaining light from an optical source; and means for transmitting the light to respective nerves of each of a plurality of inner-ear balance organs of an animal.

In some embodiments of the apparatus, the means for transmitting includes means for transmitting different amounts of the light through optical fibers to stimulate respective nerves of each of the plurality of inner-ear balance organs. In some embodiments, the means for transmitting includes means for transmitting different wavelengths of the light to stimulate respective nerves of each of the plurality of inner-ear balance organs. In some embodiments, the means for obtaining light includes a self-contained IR laser implantable device. In some embodiments, the means for obtaining light includes a self-contained battery-powered implantable device.

In some embodiments, the animal is a human person, and the apparatus further includes means for sensing a condition that affects balance, and wherein the means for transmitting includes means for transmitting different light signals, based on the sensed condition, to each of a plurality of different balance-sense organs to provide the person sense-of-balance nerve stimulation.

In other embodiments, the present invention provides a method that includes obtaining light from an optical source; transmitting the light through an optical fiber to respective nerves of an animal; and detecting electrical signals using conductors attached to the optical fiber. In some embodiments, the transmitting includes transmitting different amounts of the light through a plurality of waveguides, at least one of which is in the optical fiber, to stimulate respective nerves of each of a plurality of inner-ear balance organs. In some embodiments, the transmitting includes transmitting different wavelengths of the light to stimulate respective nerves of each of a plurality of inner-ear balance organs. In some embodiments, the obtaining light includes implanting a self-contained IR laser device. In some embodiments, the obtaining light includes implanting a self-contained battery-powered device. In some embodiments, the animal is a human person. Some embodiments further include sensing a condition that affects balance using the conductors attached to the optical fiber, and wherein the transmitting includes transmitting different light signals to each of a plurality of different balance-sense organs to provide the person sense-of-balance nerve stimulation.

In other embodiments, the present invention provides an apparatus that includes an optical source; an optical transmission medium operatively coupled to the optical source and configured to transmit light from the optical source to respective nerves of each of one or more organs of an animal; an electrical amplifier; and an electrical transmission medium integral with the optical transmission medium and operatively coupled to the electrical amplifier, wherein the electrical transmission medium is configured to transmit an electrical signal from the respective nerves to the electrical amplifier. In some embodiments, the optical transmission medium includes a plurality of optical waveguides, and the optical source couples different amounts of the light through the plurality of optical waveguides to stimulate different respective nerves of each of the plurality of inner-ear balance organs. In some embodiments, the optical source couples different wavelengths of the light to stimulate different respective nerves of each of the plurality of inner-ear balance organs. In some embodiments, the optical source includes a self-contained implantable IR laser device. In some embodiments, the optical source includes a self-contained battery-powered device. In some embodiments, the animal is a human person. Some embodiments further include at least one sensor configured to sense a condition that affects balance, and wherein the optical transmission medium transmits different light signals, based on the sensed condition, to each of a plurality of different balance-sense organs to provide the person sense-of-balance nerve stimulation.

In other embodiments, the present invention provides an apparatus that includes an optical source operable to emit light; optical fiber means for transmitting the light to respective nerves of an animal; and means, attached to the optical fiber, for detecting electrical signals. In some embodiments, the optical fiber means for transmitting includes means for transmitting different amounts of the light to stimulate respective nerves of each of the plurality of inner-ear balance organs. In some embodiments, the optical fiber means for transmitting includes means for transmitting different wavelengths of the light to stimulate respective nerves of each of the plurality of inner-ear balance organs. In some embodiments, the means for obtaining light includes a self-contained IR laser implantable device. In some embodiments, the means for obtaining light includes a self-contained battery-powered implantable device. In some embodiments, the animal is a human person, and the apparatus further includes means for sensing a condition that affects balance, and wherein the means for transmitting includes means for transmitting different light signals, based on the sensed condition, to each of a plurality of different balance-sense organs to provide the person sense-of-balance nerve stimulation.

In some embodiments, the present invention provides a method that includes obtaining light from an optical source; transmitting the light through an optical fiber between a tissue of an animal and an optical transducer; and detecting electrical signals using conductors attached to the optical fiber.

In some embodiments of the method, the transmitting includes transmitting different amounts of the light through a plurality of waveguides, at least one of which is in the optical fiber, to stimulate respective nerves of each of a plurality of inner-ear balance organs.

In some embodiments of the method, the transmitting includes transmitting different wavelengths of the light to stimulate respective nerves of each of a plurality of inner-ear balance organs.

In some embodiments of the method, the obtaining light includes implanting a self-contained IR laser device.

In some embodiments of the method, the obtaining light includes implanting a self-contained battery-powered device.

In some embodiments of the method, the animal is a human person.

Some embodiments further include sensing a condition that affects balance using the conductors attached to the optical fiber, and wherein the transmitting includes transmitting different light signals to each of a plurality of different balance-sense organs to provide the person sense-of-balance nerve stimulation.

In some embodiments, the present invention provides an apparatus that includes an optical source; an optical transmission medium operatively coupled to the optical source and configured to transmit light from the optical source to respective nerves of each of one or more organs of an animal; an electrical amplifier; and an electrical transmission medium integral with the optical transmission medium and operatively coupled to the electrical amplifier, wherein the electrical transmission medium is configured to transmit an electrical signal from the respective nerves to the electrical amplifier.

In some embodiments of the apparatus, the optical transmission medium includes a plurality of optical waveguides, and the optical source couples different amounts of the light through the plurality of optical waveguides to stimulate different respective nerves of each of the plurality of inner-ear balance organs.

In some embodiments of the apparatus, the optical source couples different wavelengths of the light to stimulate different respective nerves of each of the plurality of inner-ear balance organs.

In some embodiments of the apparatus, the optical source includes a self-contained implantable IR laser device.

In some embodiments of the apparatus, the optical source includes a self-contained battery-powered device.

In some embodiments of the apparatus, the animal is a human person.

Some embodiments further include at least one sensor configured to sense a condition that affects balance, and wherein the optical transmission medium transmits different light signals, based on the sensed condition, to each of a plurality of different balance-sense organs to provide the person sense-of-balance nerve stimulation.

In some embodiments, the present invention provides an apparatus that includes an optical source operable to emit light; optical fiber means for transmitting the light to respective nerves of an animal; and means, attached to the optical fiber, for detecting electrical signals.

In some embodiments of the apparatus, the optical fiber means for transmitting includes means for transmitting different amounts of the light to stimulate respective nerves of each of the plurality of inner-ear balance organs.

In some embodiments of the apparatus, the optical fiber means for transmitting includes means for transmitting different wavelengths of the light to stimulate respective nerves of each of the plurality of inner-ear balance organs.

In some embodiments of the apparatus, the means for obtaining light includes a self-contained IR laser implantable device.

In some embodiments of the apparatus, the means for obtaining light includes a self-contained battery-powered implantable device.

In some embodiments of the apparatus, the animal is a human person, and the apparatus further comprises means for sensing a condition that affects balance, and wherein the means for transmitting includes means for transmitting different light signals, based on the sensed condition, to each of a plurality of different balance-sense organs to provide the person sense-of-balance nerve stimulation.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method for optically stimulating a nerve-cell tissue of an animal and electrically stimulating the tissue of the animal in order to elicit an electrical nerve-action-potential response, the method comprising:
    obtaining a series of light-signal pulses for each of a plurality of optical-signal channels from an optical source, wherein each series of light-signal pulses is suitable to optically stimulate the tissue of the animal to elicit the electrical response;
    providing an electro-optic fiber bundle having a first plurality of optical waveguides and a first plurality of electrical conductors, wherein the electro-optic fiber bundle is operatively coupled to the optical source and configured to transmit the series of light-signal pulses obtained from the optical source;
    providing an integrated electro-optical substrate having a first surface that extends in two dimensions, wherein the substrate includes a second plurality of laterally spaced optical waveguides and a first plurality of exposed electrodes, wherein the providing of the substrate includes extending the laterally spaced second plurality of optical waveguides across the two dimensions of the substrate;
    optically coupling the substrate to an end of the electro-optic fiber bundle
    receiving the series of light-signal pulses from the electro-optic fiber bundle into the second plurality of optical waveguides;
    conducting electrical signals between the first plurality of electrical conductors of the electro-optic fiber bundle and the first plurality of exposed electrodes on the substrate;
    aligning the substrate such that the obtained series of light-signal pulses leaves the second plurality of optical waveguides and are directed toward the tissue of the animal;
    transmitting the series of light-signal pulses of each one of the plurality of optical-signal channels through a corresponding one of the first plurality of optical waveguides of the electro-optic fiber bundle and through a corresponding one of the second plurality of optical waveguides between the optical source and the tissue of the animal;
    optically stimulating the electrical nerve-action-potential response in the tissue of the animal using the transmitted series of light-signal pulses;
    generating an electrical-stimulation signal configured to provide electrical stimulation of the tissue of the animal;
    transmitting electrical signals corresponding to the electrical-stimulation signal using the first plurality of electrical conductors and the first plurality of exposed electrodes; and
    electrically stimulating the tissue of the animal using the transmitted electrical signals.

2. The method of claim 1, wherein the optical source is contained within a battery-powered electro-optic stimulation device, the method further comprising:
    implanting the electro-optic stimulation device, the electro-optic fiber bundle, and the substrate in the animal such that the electro-optic fiber bundle runs from the electro-optic stimulation device at a first end of the electro-optic fiber bundle to the substrate at a second, opposite end of the electro-optic fiber bundle.

3. The method of claim 1, wherein the transmitting of the series of light-signal pulses of each one of the plurality of optical-signal channels includes transmitting different wavelengths of the series of light signal pulses to stimulate respective nerves of each of a plurality of inner-ear balance organs.

4. The method of claim 1, further comprising:
    helically wrapping a flex substrate around the electro-optic fiber bundle, wherein the flex substrate is patterned with a plurality of electrical lines, wherein the plurality of electrical lines includes the first plurality of electrical conductors, and wherein a first subset of the plurality of electrical lines are electrical conductors for signal and a second subset of the plurality of electrical lines supply power.

5. The method of claim 1, wherein the providing of the electro-optic fiber bundle includes depositing the first plurality of electrical conductors as a metal film on the electro-optic fiber bundle.

6. The method of claim 1, wherein the providing of the electro-optic fiber bundle includes surrounding the first plurality of electrical conductors with an insulator layer, and depositing a co-axial metal-film shield layer on the insulator layer.

7. The method of claim 1, wherein the first plurality of electrical conductors includes a first electrical conductor and a second electrical conductor, the method further comprising:
    electrically isolating the first electrical conductor from the second electrical conductor.

8. The method of claim 1, further comprising:
    amplifying the elicited electrical nerve-action-potential response to form an amplified electrical signal; and
    transmitting the amplified electrical signal.

9. The method of claim 1, wherein the optically stimulating of the electrical nerve-action-potential response in the tissue of the animal includes optically stimulating a cochlear tissue of the animal by transmitting the series of light-signal pulses from some of the plurality of optical-signal channels through a first subset of the second plurality of optical waveguides, and optically stimulating a vestibular tissue of the animal by transmitting the series of light-signal pulses from some of the plurality of optical-signal channels through a second subset of the second plurality of optical waveguides.

10. An apparatus for optical stimulation of a nerve-cell tissue of an animal and for electrical stimulation of the tissue of the animal in order to elicit an electrical nerve-action-potential response, the apparatus comprising:
- an optical source operable to emit a series of light-signal pulses for each of a plurality of optical-signal channels, wherein each series of light-signal pulses is configured to optically stimulate the tissue of the animal to elicit the electrical response;
- an electro-optic fiber bundle that includes a first plurality of optical waveguides and a first plurality of electrical conductors, wherein the electro-optic fiber bundle is operatively coupled to the optical source and configured to transmit the series of light-signal pulses emitted from the optical source; and
- an integrated electro-optical substrate that includes a first surface that extends in two dimensions, wherein the substrate further includes a second plurality of laterally spaced optical waveguides and a first plurality of exposed electrodes, wherein the laterally spaced second plurality of optical waveguides extend across the two dimensions of the substrate, wherein the substrate is connected to an end of the electro-optic fiber bundle and configured to receive the transmitted series of light-signal pulses from the electro-optic fiber bundle into the second plurality of optical waveguides and to conduct electrical signals between the first plurality of electrical conductors of the electro-optic fiber bundle and the first plurality of exposed electrodes on the substrate, wherein the substrate is configured to output the transmitted series of light-signal pulses from the second plurality of optical waveguides toward the tissue of the animal, and wherein the substrate is configured to output the conducted electrical signals from the first plurality of exposed electrodes toward the tissue of the animal.

11. The apparatus of claim 10, wherein the optical source is contained within a battery-powered electro-optic stimulation device, and wherein the electro-optic stimulation device, the electro-optic fiber bundle, and the substrate are configured to be implanted in the animal such that the electro-optic fiber bundle runs from the electro-optic stimulation device at a first end of the electro-optic fiber bundle to the substrate at a second, opposite end of the electro-optic fiber bundle.

12. The apparatus of claim 10, wherein the optical source is configured to couple different wavelengths of the series of light signal pulses to stimulate respective nerves of each of a plurality of inner-ear balance organs.

13. The apparatus of claim 10, further comprising a flex substrate that is helically wrapped around the electro-optic fiber bundle, wherein the flex substrate is patterned with a plurality of electrical lines, wherein the plurality of electrical lines includes the first plurality of electrical conductors, and wherein a first subset of the plurality of electrical lines are electrical conductors for signal and a second subset of the plurality of electrical lines supply power.

14. The apparatus of claim 10, wherein the first plurality of electrical conductors are deposited as a metal film on the electro-optic fiber bundle.

15. The apparatus of claim 10, wherein the electro-optic fiber bundle includes:
- an insulator layer that surrounds the first plurality of electrical conductors; and
- a co-axial metal-film shield layer deposited on the insulator layer.

16. The apparatus of claim 10, wherein the animal is a human person, the apparatus further comprising:
- at least one sensor configured to sense a condition that affects balance, and wherein the substrate is configured to output a different series of light-signal pulses, based on the sensed condition, to each of a plurality of different balance-sense organs to provide the person sense-of-balance nerve stimulation.

17. The apparatus of claim 10, further comprising:
- a second plurality of electrical conductors;
- an electrical amplifier operatively coupled to the second plurality of electrical conductors, wherein the amplifier is configured to amplify the elicited electrical nerve-action-potential response to form an amplified electrical signal, and wherein the amplified electrical signal is transmitted by the second plurality of electrical conductors.

18. The apparatus of claim 10, wherein the substrate is further configured to output the transmitted series of light-signal pulses from some of the plurality of optical-signal channels through a first subset of the second plurality of optical waveguides toward cochlear tissue of the animal and to output the transmitted series of light-signal pulses from some of the plurality of optical-signal channels through a second subset of the second plurality of optical waveguides toward vestibular tissue of the animal.

19. An apparatus for optically stimulating a nerve-cell tissue of an animal and for electrically stimulating the tissue of the animal in order to elicit an electrical nerve-action-potential response, the method comprising:
- an optical source operable to emit a series of light-signal pulses for each of a plurality of optical-signal channels from, wherein each series of light-signal pulses is suitable to optically stimulate the tissue of the animal to elicit the electrical response;
- fiber-bundle means for transmitting the series of light-signal pulses of the plurality of optical-signal channels from the optical source toward the tissue of the animal and for transmitting electrical-stimulation signals toward the tissue of the animal;
- substrate means for transmitting, optically coupled and electrically coupled to the fiber-bundle means for transmitting, the series of light-signal pulses of the plurality of optical-signal channels from the fiber-bundle means to the tissue of the animal and for transmitting the electrical signals from the fiber-bundle means to the tissue of the animal; and
- means for aligning the substrate means for transmitting the series of light-signal pulses to direct the transmitted series of light-signal pulses to the tissue of the animal.

20. The apparatus of claim 19, further comprising flex means for helically wrapping around the fiber-bundle means for transmitting, wherein the flex means is patterned with a plurality of electrical lines configured to transmit the electrical stimulation signals toward the tissue of the animal.

21. The apparatus of claim 19, wherein the optical source is configured to couple different wavelengths of the series of light signal pulses to stimulate respective nerves of each of a plurality of inner-ear balance organs.

22. The apparatus of claim 19, further comprising:
means for amplifying the elicited electrical nerve-action-potential response to form an amplified electrical signal; and
means for transmitting the elicited electrical response from the tissue of the animal to the means for amplifying.

23. The apparatus of claim 19, wherein the substrate means for transmitting includes means for transmitting the series of light-signal pulses of some of the plurality of optical-signal channels to a cochlear tissue of the animal and means for transmitting the series of light-signal pulses of some of the plurality of optical-signal channels to a vestibular tissue of the animal.

* * * * *